(12) United States Patent
Liu et al.

(10) Patent No.: US 7,744,894 B2
(45) Date of Patent: Jun. 29, 2010

(54) METHOD OF TREATING MULTIPLE SCLEROSIS AND RELATED T-CELL INITIATED TISSUE DESTRUCTION BY ADMINISTERING HSA/CD24

(76) Inventors: Yang Liu, 1474 Brighton Dr., Columbus, OH (US) 43220; Pan Zheng, 1474 Brighton Dr., Columbus, OH (US) 43220; Xuefeng Bai, 2719 Wellesley Dr., Columbus, OH (US) 43221

(*) Notice: Subject to any disclaimer, the term of this patent is extended or adjusted under 35 U.S.C. 154(b) by 914 days.

(21) Appl. No.: 11/129,083

(22) Filed: May 13, 2005

(65) Prior Publication Data

US 2005/0202014 A1    Sep. 15, 2005

Related U.S. Application Data

(60) Division of application No. 10/119,637, filed on Apr. 10, 2002, now abandoned, which is a continuation-in-part of application No. 09/822,851, filed on Mar. 29, 2001, now abandoned.

(60) Provisional application No. 60/192,814, filed on Mar. 29, 2000.

(51) Int. Cl.
    A61K 39/00    (2006.01)
    A61K 39/38    (2006.01)
(52) U.S. Cl. .................................. 424/185.1
(58) Field of Classification Search ............... None
    See application file for complete search history.

(56) References Cited

U.S. PATENT DOCUMENTS

| | | | |
|---|---|---|---|
| 5,225,538 A | 7/1993 | Capon | |
| 5,593,826 A | 1/1997 | Fung et al. | |
| 5,643,570 A | 7/1997 | Theofan et al. | |
| 5,952,471 A | 9/1999 | Lawson et al. | |
| 6,300,492 B1 | 10/2001 | Korneluk et al. | |
| 6,379,670 B1 | 4/2002 | Gaur et al. | |
| 6,656,466 B1 | 12/2003 | Etcheverry et al. | |
| 7,232,566 B2 | 6/2007 | June | |

FOREIGN PATENT DOCUMENTS

| | | |
|---|---|---|
| WO | 01/72325 | 10/2001 |
| WO | 2005/054810 | 6/2005 |

OTHER PUBLICATIONS

Kay, R., et al. J. Immunol. Aug. 1991;147(4):1412-1416.*
Zhou, Q., et al. PNAS. 2003;100(25):15041-15046.*
Liu, Y., et al. Trends in Immunol. 2007;28(7):315-320.*
Liu, J.Q., et al J. Immunol. 2007;178:6227-6235.*
Abstract—Gupta, "Sequence and Structural Homology Between a Mouse T Complex Protein TCP-1 and the Chaperonin Family of Bacterial Groel 60-65-KDA Heat Shock Antigen and Eukaryotic Proteins", Biochem Int. (1990) vol. 20, No. 4, pp. 833-841.

Bai et al., "The heat-stable antigen determines pathogenicity of self-reactive T cells in experimental autoimmune encephalomyelitis", The Journal of Clinical Investigation(2000) vol. 105, No. 9, pp. 1127-1232.

Wither et al., "Genetic dissection of B cell traits in New Zealand black mice. The expanded population of B cells expressing up-regulated costimulatory molecules shows linkage to Nba2", Eur. J. Immunol (2000) vol. 30, pp. 356-365.

Springer, TA, "Traffic signals for lymphocyte recirculation and leukocyte emigration: the multistep paradigm" Cell 76: 301-314 (1994).

Salamone, et al., "Antibodies recognizing CD24 LAP epitope on human T cells enhance CD28 and IL-2 T cell proliferation", J. of Leukocyte Biology, vol. 69, Feb. 2001, pp. 215-223.

Zhou, Q., et al., "Homotypic interaction of the heat-stable antigen is not responsible for its co-stimulatory actdivity for T cell clonal expansion", Eur. J. Immunol. 27: 2524-2528, (1997).

Zamvil, SS et al., "The T lymphocyte in experimental allergic encephalomyelitis", Annu. Rev. Immunol. 8: 579-621 (1990).

Wu, Y., et al., "CD28-independent induction of T helper cells and immunoglobulin class switches requires costimulation by the heat-stable antigen", J. Exp. Med. 187: 1151-1156 (1998).

Wu, TC et al., "A reassessment of the role of B7-1 expression in tumor rejectdion", J. Exp. Med. 182: 1415-1421 (1995).

Wang, Y-C., et al. "Expression of heat-stable antigen on tumor cells provides co-stimulation for tumor-specific T cell proliferation and cytotoxicity in mice", Eur. J. Immunol. 25: 1163-1167 (1995).

Vyse, TJ et al., "Genetic analysis of autoimmune disease", Cell 85: 311-318 (1996).

Vanderlugt, CL et al., "The functional significance of epitope spreading and its regulation by co-stimulatory molecules", Immunol. Rev. 164: 63-72 (1998).

Tselios et al., "Antagonistic effects of human cyclic MBP (87-99) altered peptide ligands in experimental allergic encephalomyelitis and human T-cell proliferation", J. of Medicinal Chemistry 45: 275-283, (2002).

Zarn et al. "The small cell lung cancer antigen cluster-4 and the leukocyte antigen CD24 are allelic isoforms of the same gene (CD24) on chromosome band 6q21", Cytogenet Cell Genet 70: 119-125 (1995).

Allison, J., et al., "The threshold for autoimmune T cell killing is influenced by B7-1", Eur. J. Immunol. 28: 949-960, (1998).

Baron, JL, et al., "Surface expression of alpha 4 integrin by CD4 T cells is required for their entry into brain parenchyma", J. Exp. Med. 177: 57-68 (1993).

(Continued)

Primary Examiner—G. R Ewoldt
(74) Attorney, Agent, or Firm—Polsinelli Shughart PC; Teddy C. Scott; Ron Galant

(57) ABSTRACT

Methods for blocking autoreactive T cell-initiated destruction of tissues in a mammal are provided. In one embodiment, the methods involve administering an HAS/CD24 polypeptide or fragment thereof. In some embodiments, the polypeptide or fragment is glycosylated.

6 Claims, 18 Drawing Sheets

OTHER PUBLICATIONS

Becker, KG et al., "Clustering of non-major histocompatibility complex susceptibility candidate loci in human autoimmune diseases", Proc. Natl. Acad. Sci, USA 95: 9979-9984 (1998).

Meulenbroek AJ & Zeijlemarker WP (1996) Human IgG Subclasses: Useful diagnostic markers for immunocompetence Sanquin formerly, Sections 1 through 2.3, http://www.xs4all.nl/~ednieuw/IgGsubclasses/subkl.htm, published by CLB, 1996, The Netherlands, ISBN 90-5267-011-0 Internet Page By Ed Nieuwenhuys, 14 pgs.

Chaffin, KE, et al., "Dissection of thymocyte signaling pathways by in vivo expression of pertussis toxin ADP-ribosyltransferase", EMBO J. 9: 3821-3829 (1990).

Chang, TT, et al., "Studies in B7-deficient Mice Reveal a critical role for B7 costimulation in both induction and effector phases of experimental autoimmune encephalomyelitis", J. Exp. Med. 190: 733-740 (1999).

Chong, H., et al., "Expression of B7 co-stimulatory molecules by B16 melanoma results in a natural killer cell-dependent local antitumour response, but induces T-cell-dependent systemic immunity only against B7-expressing tumours", Br. J. Cancer, 78: 1043-1050 (1998).

Crispe, IN, et al., "Expression and functional significance of the J 11 d marker on mouse thymocytes", J. Immunol. 138: 2013-2018 (1987).

Cross et al., "Long-term inhibition of murine experimental autoimmune encephalomyelitis using CTLA-4-Fc supports a key role for CD28 costimulation", J. of Clinical Investigation 95: 2783-2789, (Jun. 1995).

DeBruijn, JL et al., "Induction of heat-stable antigen-expression by phagocytosis is involved in in vitro activation of unprimed CTL by macrophages", J. Immunol. 156: 2686-2692 (1996).

Engelhardt, B., et al., "E-and P-selectin are not involved in the recruitment of inflammatory cells across the blood-brain barrier in experimental autoimmune encephalomyelitis", Blood, 90: 4459-4472 (1997).

Jefferis, R., Molecular Structure of Human IgG Subclasses, pp. 15-31, In: Shakib F, ed. The Human IgG subclasses, Pergamon press. 1990.

Kadmon, G., et al, "Nectadrin, the heat-stable antigen, is a cell adhesion molecule", J. Cell. Biol 188: 1245-1253 (1992).

Kerlero de Rosbo, N., et al., "Chronic relapsing experimental autoimmune encephalomyelitis with a delayed onset and an atypical clinical course, induced in PL/J mice by myelin oligodendrocyte glycoprotein (MOG)-derived peptide: preliminary analysis of MOG T cell epitopes", Eur. J. Immunol. 25: 985-993 (1995).

Lafaille, JJ et al., "Myelin basic protein-specific T helper 2 (th2) cells cause experimental autoimmune encephalomyelitis in immunodeficient hosts rather than protect them from the disease", J. Exp. Med 186: 307-312 (1997).

Liu, Y, et al., "Co-stimulation of murine CD4 T cell growth: cooperation between B7 and heat-stable antigen", Eur. J. Immunol. 22: 2855-2859 (1992).

Liu, Y, et al., "Heat stable antigen is a costimulatory molecule for CD4 T cell growth", J. Exp. Med. 175: 437-445 (1992).

Liu, Y, et al., "Distinct costimulatory molecules are required for the induction of effector and memory cytotoxic T lymphocytes", J. Exp. Med. 185: 251-262 (1997).

Mendel, I., et al., "A myelin oligodendrocyte glocyprotein peptide induces typical chronic experimental autoimmune encephalomyelitis in H-2b mice: fine specificity and T cell receptor V beta expression of encephalitogenic T cells", Eur. J. Immunol. 25: 1951-1959 (1995).

Miller, SD et al., "Evolution of the T-cell repertoire during the course of experimental immune-mediated demyelinating diseases", Immunol. Rev. 144: 225-244 (1995).

Miller, RA et al., "Early activation defects in T lymphocytes from aged mice", Immunol. Rev. 160: 79-90 (1997).

Oliveira-dos-Santos, AJ et al., "CD28 costimulation is crucial for the development of spontaneous autoimmune encephalomyelitis", J. Immunol. 162: 4490-4495, (1999).

Ramarathinam, L., et al. "T cell costimulation by B7/BB1 induces CD8 T cell-dependent tumor rejectdion: an important role of B7/BB1 in the induction, recruitment, and effector function of antitumor T cells", J. Exp. Med. 179: 1205-1214 (1994).

Rougon, G. et al., "The murine heat-stable antigen: a differentiation antigen expressed in both the hematolymphoid and neural cell lineages", Eur. J. Immunol. 21: 1397-1402 (1991).

Sarma, S., et al., "Cytotoxic T lymphocytes to an unmutated tumor rejection antigen P1A: normal development but restrained effector function in vivo", J. Exp. Med. 189: 811-820 (1999).

Carter and Rodriguez, "Immunosupressive treatment of Multiple Sclerosis," Mayo Clinic Proc. 64: 664 (1989).

Collins, "Positional Cloning: Let's not call it reverse anymore" Nature Genetics 1: 3-6 (Apr. 1992).

Eisenhaber, B , et al. "Sequence properties of GPI-anchored proteins near the omega-site: constraints for the polypeptide binding site of the putative transamidase," Protein Eng 11 (12) 1155-61 (1998).

Englund, P. T., "The Structure and Biosynthesis of Glycosyl Phosphatidylinositol Protein Anchors", Annu Rev Biochem 62:121-38 (1993).

Fischer, G.F., et al., "Signal transduction in mymphocyctic and myeloid cells via CD24, a new member of phosphoinositol-anchored membrane molecules," J. Immun. 144:638-641 (Jan. 15, 1990).

Noseworthy, J. H. "Progress in determining the causes and treatment of multiple sclerosis," Nature 399 Supp., A40-47 (Jun. 24, 1999).

Udenfriend, S. et al., "How glycosyl-phosphatidylinositol-anchored membrane proteins are made", Annu Rev Biochem 64:563-91 (1995).

Springer, T, et al., "Monoclonal xenogeneic antibodies to murine cell surface antigens: identification of novel leukocyte differentiation antigens", Eur. J. Immunol 8: 539-551 (1978).

Soldevila, G., et al., "Breaking immunologic ignorance to an antigenic peptide of simian virus 40 large T antigen", J. Immunol. 155: 5590-5600 (1995).

Shi, FD et al., "Differential requirements for CD28 and CD40 ligand in the induction of experimental autoimmune myasthenia gravis", Eur. J. Immunol. 28: 3587-3593 (1998).

Shahinian, A., et al., "Differential T cell costimulatory requirements in CD28-deficient mice", Science 261: 609-612 (1993).

Schlaeger, TM et al., "Uniform vascular-endothelial-cell-specific gene expression in both embryonic and adult transgenic mice", Proc. Natl. Acad. Sci USA 94: 3058-63 (1997).

Zhou Q et al. CD24 is a genetic modifier for risk and progression of multiple sclerosis. Proc Natl Acad Sci USA, 2003;100(25):15041-6.

Mix E et al. Animal models of multiple sclerosis for the development and validation of novel therapies—potential and limitations. J Neurol. Dec. 2008;255 Suppl 6:7-14.

Steinman L and Zamvil SS. How to successfully apply animal studies in experimental allergic encephalomyelitis to research on multiple sclerosis. Ann Neurol. Jul. 2006;60(1):12-21.

Park JE et al. Placenta growth factor. Potentiation of vascular endothelial growth factor bioactivity, in vitro and in vivo, and high affinity binding to Flt-1 but not to Flk-1/KDR. J Biol Chem. Oct. 14, 1994;269(41):25646-54.

Aigner et al. Heat stable antigen (mouse CD24) supports myeloid cell binding to endotelial and platelet P-selectin, International Immunology (Oct. 1995) vol. 7, No. 10, pp. 1557-1565.

Aigner, et al. "CD24 mediates rolling of breast carcinoma cells on P-selectin"The FASEB Journal (1998), vol. 12, pp. 1241-1251.

Ashkenazi, et al, "Protection Against Endotoxic Shock by a Tumor Necrosis Factor Receptor Immunoadhesin", Proc. Natl. Acad. Sci. (1991) vol. 88, pp. 10535-10539.

Bai, et al, CD24 controls expansion and persistence of autoreactive T cells in the central nervous system during experimental autoimmune encephalomyelitis, The Journal of Experimental Medicine (Aug. 16, 2004) vol. 200, No. 4, pp. 447-458.

Burton, Aspects of the Molecular Structure of IgG Subclasses, monogr. Allergy, vol. 19, pp. 7-35 (Karger, Basel 1986).

Chen et al, Establishment and characterization of cloned CD4-CD8-alphabeta-T cell receptor (TCR)-bearing autoreactive T cells from autoimmune NZB x NZW F1 mice, Clinical and Experimental Immunology, (Apr. 1997) vol. 108, No. 1, pp. 52-57.

Enk et al. Heat-stable antigen is an important costimulatory molecule on epidermal Langerhans' cells, Journal of Immunology (Apr. 1, 1994) vol. 152, No. 7, pp. 3264-3270.

Erdmann et al. Heat-stable antigen is expressed by murine keratinocytes and delivers costimulatory signals in T-cell activation, Experimental Dermatology (Oct. 1995) vol. 4, No. 5, pp. 291-296.

Hahne et al, The heat-stable antigen can alter very late antigen 4-mediated adhesion, The Journal of Experimental Medicine, (Apr. 1, 1994) vol. 179, No. 4, pp. 1391-1395.

Hubbe et al. Heat-stable antigen/CD24 on mouse T lymphocytes: evidence for a costimulatory function, European Journal of Immunology (Mar. 1, 1994) vol. 24, No. 3, pp. 731-737.

Kay, et al. "CD24, A Signal Transducer Modulating B Cell Activation Responss, is a Very Short Peptide with a Glycosyl Phosphatidylinositol Membrane Anchor", The Journal of Immunology (1991) vol. 147, No. 4, pp. 1412-1416.

Miller, et al. "Specific Interaction of Lymphocyte Function-associated antigen 3 with CD2 Can Inhibit T Cell Responses", J. Exp. Med. (1993) vol. 178, pp. 211-222.

Nielsen et al, Constitutive expression of transgenic heat stable antigen (mCD24) in lymphocytes can augment a secondary antibody response, International Immunology (Nov. 1993) vol. 5, No. 11, pp. 1355-1364.

Nielsen et al. Altered erythrocytes and a leaky block in B-cell development in CD24/HSA-deficient mice (Feb. 1, 1997), vol. 89, No. 3, pp. 1058-1067.

Pawliuk et al. Selection of retrovirally transduced hematopioetic cells using CD24 as a marker of gene transfer, Blood (Nov. 1, 1994) vol. 84, No. 9, pp. 2868-2877.

Stinissen et al. Autoimmune pathogenesis of multiple sclerosis: role of autoreactive T lymphocytes and new immunotherapeutic strategies, Critical Reviews in Immunology (1997) vol. 17, No. 1, pp. 33-75.

Wenger et al. B-cell maturation in chimaeric mice deficient for the heat stable antigen (HSA/mouse CD24), Transgenic Research (May 1995) vol. 4, No. 3, pp. 173-183.

* cited by examiner

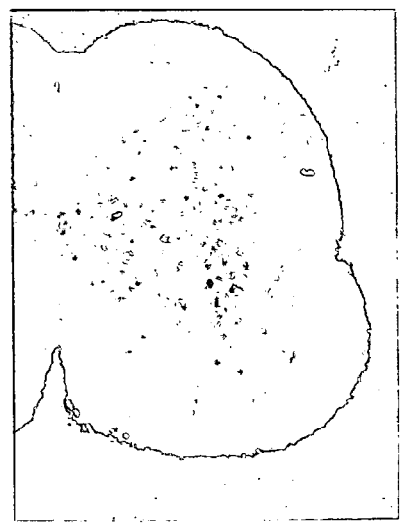
Fig. 3a HSA(-/-) > HSA(-/-)
Fig. 3b WT > HSA(-/-)
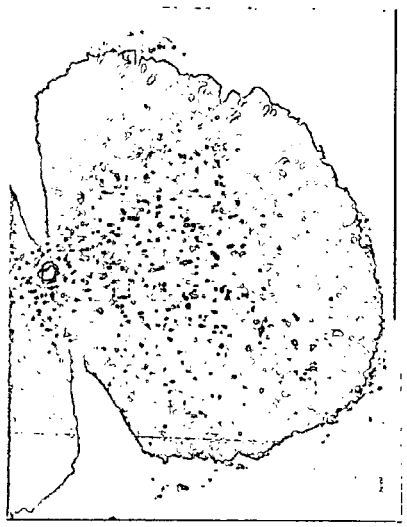
Fig. 3c HSA(-/-) > WT
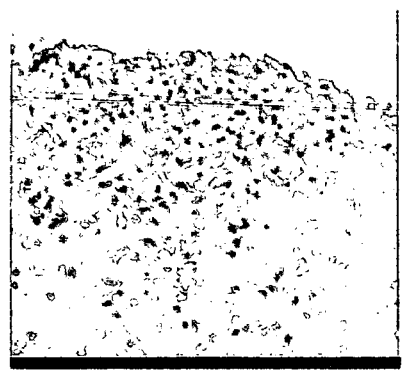
Fig. 3d WT > WT

MURINE HSA POLYPEPTIDE, SEQ ID NO. 1

```
  1 mgramvarlg lgllllalll ptqiycnqts vapfpgnqni saspnpsnat
 51 trgggsslqs tagllalsls llhlyc
```

Figure 7

Human CD24 polypeptide sequence, SEQ ID NO.:2 mgramvarlglglllalllptqiyssetttgtssnssqstsnsglapnptnattkva
ggalqstaslfv vslsllhlys

Figure 8

Rat CD24 polypeptide sequence, SEQ ID NO.:3

1 mgramvvrlg lgllllalll ptqiycnqts vapfsgnqsi saapnptnat trsgcsslqs 61 tagllalsls llhlyc

Figure 9

FUSION GENE DNA sequence 1494 bp, SEQ ID NO.:4

ATGGGCAGAGCGATGGGGGCCAGGCTAGGGCTGGGGTTGCTGCTTCTGGCACTGCTCCTACCCACGCAGA
TTTACTGCAACCAAACATCTGTTGCACCGTTTCCCGGTAACCAGAATATTTCTGCTTCCCCAAATCCAAG
TAACGCTACCACCAGAGATCCCGAGGGTGAGTACTAAGCTAGCT*TCAGCGCTCCTGCCTGGACGCATCCC*
*GGCTATGCAGCCCCAGTCCAGGGCAGCAAGGCAGGCCCCGTCTGCCTCTTCACCCGGAGCCTCTGCCCGC*
*CCCACTCATGCTCAGGGAGAGGGTCTTCTGGCTTTTTCCCAGGCTCTGGGCAGGCACAGGCTAGGTGCCC*
*CTAACCCAGGCCCTGCACACAAGGGGCAGGTGCTGGGCTCAGACCTGCCAAGAGCCATATCCGGGAGGA*
*CCCTGCCCCTGACCTAAGCCCACCCCAAAGGCCAAACTCTCCACTCCCTCAGCCGGACACCTTCTCTCCT*
*CCCAGATTCCAGTAACTCCCAATCTTCTCTCTGCAGAGCCCAAATCTTGTGACAAAACTCACACATGCCC*
*ACCGTGCCCAGGTAAGCCAGCCCAGGCCTCGCCCTCCAGCTCAAGGCGGGACAGGTGCCCTAGAGTAGCC*
*TGCATCCAGGGACAGGCCCCAGCCGGGTGCTGACACGTCCACCTCCATCTCTTCCTCAGCACCTGAACTC*
*CTGGGGGGACCGTCAGTCTTCCTCTTCCCCCCAAAACCCAAGGACACCCTCATGATCTCCCGGACCCCTG*
AGGTCACATGCGTGGTGGTGGACGTGAGCCACGAAGACCCTGAGGTCAAGTTCAACTGGTACGTGGACGG
CGTGGAGGTGCATAATGCCAAGACAAAGCCGCGGGAGGAGCAGTACAACAGCACGTACCGGGTGGTCAGC
GTCCTCACCGTCCTGCACCAGGACTGGCTGAATGGCAAGGAGTACAAGTGCAAGGTCTCCAACAAAGCCC
TCCCAGCCCCCATCGAGAAAACCATCTCCAAAGCCAAAGGTGGGACCCGTGGGGTGCGAGGGCCACATGG
*ACAGAGGCCGGCTCGGCCCACCCTCTGCCCTGAGAGTGACCGCTGTACCAACCTCTGTCCTACAGGGCAG*
*CCCCGAGAACCACAGGTGTACACCCTGCCCCCATCCCGGGATGAGCTGACCAAGAACCAGGTCAGCCTGA*
*CCTGCCTGGTCAAAGGCTTCTATCCCAGCGACATCGCCGTGGAGTGGGAGAGCAATGGGCAGCCGGAGAA*
CAACTACAAGACCACGCCTCCCGTGCTGGACTCCGACGGCTCCTTCTTCCTCTACAGCAAGCTCACCGTG
GACAAGAGCAGGTGGCAGCAGGGGAACGTCTTCTCATGCTCCGTGATGCATGAGGCTCTGCACAACCACT
ACACGCAGAAGAGCCTCTCCCTGTCTCCGGGTAAATGAGTGCGACGGCCGGCAAGCCCCGCTCCCCGGGC
TCTCGCGGTCGCACGAGGATGCTT

Predicted cDNA sequence 864 bp (after splicing of the introns) in the IgG1Fc

ATGGGCAGAGCGATGGGGGCCAGGCTAGGGCTGGGGTTGCTGCTTCTGGCACTGCTCCTACCCACGCAGA
TTTACTGCAACCAAACATCTGTTGCACCGTTTCCCGGTAACCAGAATATTTCTGCTTCCCCAAATCCAAG
TAACGCTACCACCAGAGATCCCGAGGAGCCCAAATCTTGTGACAAAACTCACACATGCCCACCGTGCCCA
GGCACCTGAACTCCTGGGGGGACCGTCAGTCTTCCTCTTCCCCCCAAAACCCAAGGACACCCTCATGATC
TCCCGGACCCCTGAGGTCACATGCGTGGTGGTGGACGTGAGCCACGAAGACCCTGAGGTCAAGTTCAACT
GGTACGTGGACGGCGTGGAGGTGCATAATGCCAAGACAAAGCCGCGGGAGGAGCAGTACAACAGCACGTA
CCGGGTGGTCAGCGTCCTCACCGTCCTGCACCAGGACTGGCTGAATGGCAAGGAGTACAAGTGCAAGGTC
TCCAACAAAGCCCTCCCAGCCCCCATCGAGAAAACCATCTCCAAAGCCAAAGGCAGCCCCGAGAACCACA
GGTGTACACCCTGCCCCCATCCCGGGATGAGCTGACCAAGAACCAGGTCAGCCTGACCTGCCTGGTCAAA
GGCTTCTATCCCAGCGACATCGCCGTGGAGTGGGAGAGCAATGGGCAGCCGGAGAACAACTACAAGACCA
CGCCTCCCGTGCTGGACTCCGACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACAACCACTACACGCAGAAGAGC
CTCTCCCTGTCTCCGGGTAAATGA

Predicted AA sequence fusion protein  287 AA

MGRAMGARLGLGLLLLALLLPTQIYCNQTSVAPFPGNQNISASPNPSNATTRDPE*EPKSCDKTHT*
*CPPCPAPELLGGPSVFLFPPKPKDTLMISRTPEVTCVVVDVSHEDPEVKFNWYVDGVEVHNAKTKPRE*
*EQYNSTYRVVSVLTVLHQDWLNGKEYKCKVSNKALPAPIEKTISKAKGQPREPQVYTLPPSRDELTKNQ*
*VSLTCLVKGFYPSDIAVEWESNGQPENNYKTTPPVLDSDGSFFLYSKLTVDKSRWQQGNVFSCSVMHE*
*ALHNHYTQKSLSLSPGKZ*

Figure 10

```
                                                    ttcaggaatt cagaatttga
      aatgcggcta agagaacaat gtggggaaaa aagagtctta gggcggatca gggactggag
      agtgtaattc agtggtggag cgtgaatact tagtgtccct aagaccctgt gtttggcttc
      tacctgcagc tacagagact attatctgct tgagtgttat tacagagtgc aaatggagat
      agctgtggat ggttctgaaa tttatctgtg atttctttt ccttatttat tttagattta
      ct(HUCD24) agatttactc gagtgaaaca caactggaa cttcaagtaa ctcctcccag
       agtacttcca acactgggtt ggccccaaat ccaactaatg ccaccaccaa ggcggctggt
       ggtgccctgc agtcaacagc cagtctcttc gtggtctcac tctctcttct gcatctctac
       tcttaagaga ctcaggccaa gaaacgtctt ctaaacttcc ccatcttcta aacccaatcc
       aaatggcgtc tggaagtcca atg
        (The following numbering based on X72910)  aagtccaatg tgatcaggaa
6001 gaaacaggtc cacctcgaat tggctgttac catatctcaa cagaaaacac ggagaattcg
6061 aaattcgacg ggattaaagg acgcgtgaaa ggtttgagag aagagagatg ccgctattga
6121 atctgctgga gttttacatc ccaagatgaa gacagcattc agaattgatg tgatttcctt
6181 gaatgtggct taggaaatgt ggacacttaa aactctcact tgaaattggg cacaggtttg
6241 atgtagagat aaggacgggg tgcggaatgg agaccatttt tgtcattgat tcatctgacc
6301 gataaggcca tagtgcagtt aggtgatatt cgaagcttct tgatgctct ttatgtatat
6361 gttggaagga actaccaggc gttgctttaa attcccaatg tgttgtttcg ttactactaa
6421 tttaataccg taagctctag gtaaagttcc atgttgttga actctgactg ttctctttgg
6481 aattgaacgt tttgcatcct cctcctgtgg ctttaggtct gacattgtat ttgacctta
6541 ctagtaatta acatgtgcca ggcaatggtg gattggaacc catcccaag tccagccacc
6601 actgaataaa tctgatttca aaagtcaaac agtagacatt tcccattgtc gtttctcact
6661 caccacaagc accaaattca ctagagtaca ctggttccag agagcagaat catgttggcc
6721 ttggctaatt tcaaaatgct gtcttttact ttggtatatg ttgagggctt tcataattt
6781 aaagtgtgtt ctgttagcaa ggcaaaaatt atgagtctta attctacagg caaatatgca
6841 aaggagccaa aactgtaaac ccagcatttg ggatgtgaag actgaagct aactctcatt
6901 gaattcacaa agtcttttat acgatttctg tacatacttt ttttttttt aagagaaaaa
6961 caaacggtgg atcagaatag ccacgtttgg aatactttgg ttatccattc atattttag
7021 atagttattg gtcctgtgcc tgaaggggg cttggttcta ccgtaagttt ttccaatttc
7081 cttgatatac ataccttc taaaacctag acatttcctg aaaaaaatct tttgttcgca
7141 tggtcacaca ctgatgctta cccgtacagt agtcttgata accagagtca tttctccat
7201 ctttagaaac cttcctggga agaaggagag ctcacagacc cgaagctact gtgtgtgtga
7261 atgaacactc cccttgcctc acctgaat gctgtacatc tatttgattg taaattgtgt
7321 ttgtgtattt atgctttgat tcatagtaac ttctcatgtt atggaattga tttgcattga
7381 acacaaactg taaataaaag aaagaaatgg cggagagagc agtctgttga atttatttac
7441 ttacttttta aaaagactta tttattttat gtatgtgagt atatcgaagt tgttttcaga
7501 cacaccagaa gagggtatca gatggttgtg agccactgtg tggttgctgg gaattgaact
7561 caggacc
```

FIGURE 11B

```
   1 tctagaaggg tagccagtgc tcttaaccac tgagccatct ctccagcccc cagtctgttg
  61 aatttaaagt gtttcttgag caataattat gggtgatcat ggctgttaag ggatatatct
 121 tgttctacta actagaacat tacatgctgt ctattttga aaggccagct agcagcaggt
 181 ttggtttcct cccaaagctg ctccccccct tccaagtgct gggaataaag gcgtgtgcct
 241 ccacgcctgt ctctagttga catctttaag cttttaaggt tgtacaccta cttgctcagc
 301 aactgagagc cagctgtgtg ccaaggtacc catgactgat gaagttggct ggggagagag
 361 tctttgagat gagaggtctc tggtttgcca ggcagggctc ttaggacaac accagcaggg
 421 cagggctctg ggaccacaga ttgagaaccc acaatggcct tgaaccttag acctgaatga
 481 caggtgttgg tgggagaaca tgagcggaaa ttttcgtgga atgaacagct tctaagtcac
 541 ctctactttc tcttaccggc ccagaggtct acacctcact ttggttttct aaattggctc
 601 tcccctgctt tttccatata tcaaacacat tcctggattc ctaacatctt tactgtgatt
 661 cagggaccac cagaaagggc aggctggaaa ctgctgttct taggcagagt tccataagaa
 721 acctcaggtc tacccttaa gacttagatg atctggagct ctcttcaatg atgtctacag
 781 attgccctcc ccgctgcacc ccactccgca gccatatgaa gtatactagg ttggtgtggg
 841 ggtaactgag aactacttat tgacatgtaa actggtcacc acagttcatt gtctcagcat
 901 gttttgtctc cagatgaaca atagcctctc tctagtagag aagtgtcttg cacacaaaca
 961 gaaacatttc ccagaagtgc cagtgtcgtt cattcatcct actttggttt aagtgtctga
1021 ttgttttttg ttttggaaac tgtctcattc tgtatgtagc ctaggctggt ctcaaactta
1081 gggtggtctt acctcagtct cctgagcccc gggcttgtgt cgtcacaccc agcttttctg
1141 tgttttgttt tttggttttg ttttgttttg aaacagggtt ttgctatgtg acttaggcat
1201 actatgtagc ctgggctggc cttgaactca tggacatctg cctctgtttc ctgagagcta
1261 gagttacaga tgtgtgtcac ttatgttcac tcttagtatc ctgtgattta tgttagatat
1321 tactgaaaat tattactaaa tcttgtcagt tgtagatacg atgggagaat gta
```

FIGURE 11C

```
Query: 1984 gaagctactgtgtgtgtgaatgaacactcttttgctttattccagaatgctgtacatct 2042
              ||||||||||||||||||||||||||||||    ||||  |  |   ||  |||||||||||||||
Sbjct: 1629 gaagctactgtgtgtgtgaatgaacactccccttgcctcacacctgaatgctgtacatct 1688

Query: 2043 attttggattgtatattgtgtttgtgtatttacgctttgattcatagtaacttc-----t 2097
              ||||  ||||||||  ||||||||||||||||  |||||||||||||||||||||||        |
Sbjct: 1689 attt--gattgtaaattgtgtttgtgtatttatgctttgattcatagtaacttctcatgt 1746

Query: 2098 tatggaattgatttgcattgaacacaaactgtaaataaaa 2137
              ||||||||||||||||||||||||||||||||||||||||
Sbjct: 1747 tatggaattgatttgcattgaacacaaactgtaaataaaa 1786

Query: 1555 aggcaaaaatgtaaaggagtcaaaactacaaatcaagtatttgggaagtgaagactggaa 1614
              |||||||   |||  |||||||  |||||||||   |  ||  ||||||| ||||||||||||||||
Sbjct: 1216 aggcaaatatgcaaaggagccaaaactgtaaacccagcatttgggatgtgaagactggaa 1275

Query: 1615 gctaatttgcattaaattcacaaa--cttttatactctttctgtatatacnnnnnnnnct 1672
              ||||| |    ||||  |||||||||||   |||||||||||   ||||||||  ||||      |
Sbjct: 1276 gctaactctcattgaattcacaaagtcttttatacaatttctgtacatacttttttttttt 1335

Query: 1673 tt------aaaaaacaactatggatcagaatagccacatttggaatacttttgttatca 1726
              ||               |||||  |||     |||||||||||||||| ||||||||||||  |||  ||||||
Sbjct: 1336 tttaagagaaaaacaaacggtggatcagaatagccacgtttggaatac-tttggttatcc 1394

Query: 1727 gtcaatatttttagatagttagaacctggtcctaagcctaaaagtgggcttgattctgca 1786
              |  |||||||||||||||||||   |||||||  ||||  ||||  |||||||  ||||||  |
Sbjct: 1395 attcatatttttagatagtta----ttggtcctgtgcctgaaaggggggcttggttctacc 1450

Query: 1787 gtaaatcttttacaactgcctcgaaacacagaaacctttttaaaaatagacactcccg- 1845
              ||||  |  ||||  |||   ||  ||   |  |||  |  |||||  |||   |||||| |   ||  |
Sbjct: 1451 gtaagt-ttttccaatttccttgatatacacataccttctaaaacctagacatttcctga 1509

Query: 1846 ---aagtcttttgttcgcatggtcacacactgatgctta 1881
                 ||  ||||||||||||||||||||||||||||||||||||||
Sbjct: 1510 aaaaaatcttttgttcgcatggtcacacactgatgctta 1548

Query: 119 gctgctgctgctggcactgctcctacccacgcagattta 157
             |  ||||||||  ||||||||||||||||||||||||||||||
Sbjct: 108 gttgctgcttctggcactgctcctacccacgcagattta 146
```

FIGURE 14

METHOD OF TREATING MULTIPLE SCLEROSIS AND RELATED T-CELL INITIATED TISSUE DESTRUCTION BY ADMINISTERING HSA/CD24

REFERENCE TO RELATED APPLICATION

This application is a divisional of U.S. application Ser. No. 10/119,637, filed Apr. 10, 2002 now abandoned, which is a continuation-in-part of U.S. application Ser. No. 09/822,851 which was filed on Mar. 29, 2001 now abandoned, and claims priority to U.S. Provisional Patent Application No. 60/192,814, filed on Mar. 29, 2000. The entire disclosures of applications Ser. Nos. 10/119,637, 09/822,851, and 60/192,814, are incorporated herein by reference.

STATEMENT OF GOVERNMENT SUPPORT

This invention is supported, at least in part, by Grant No. AI32981 from the National Institute of Health, USA. The U.S. government has certain rights in this invention.

BACKGROUND OF THE INVENTION

The present invention relates to agents and methods for blocking deleterious T cell mediated immune reactions. Such reactions occur in autoimmune diseases, such as for example, multiple sclerosis (MS), rheumatoid arthritis, systemic lupus erythematosis, psoriasis, diabetes, and allergies. Such reactions also occur during rejection of transplants.

In theory, autoimmune diseases can be prevented by blocking activation of T cells and formation of autoreactive T cells. Accordingly, there are a number of studies being conducted to identify methods or agents that can be used to block activation of T cells (J Clin Invest. 1995 June; 95(6):2783-9; J Med. Chem. 2002 January 17; 45(2):275-83). Unfortunately, since patients with autoimmune diseases have already developed autoreactive T cells, these methods have limited value for treatment of autoimmune diseases. Moreover, agents that prevent systemic T cell activation often cause serious side effects. For example, treatment with agents that block activation of T cells can also render the patient more susceptible to infections and cancer. Thus, it is desirable to have new methods for treating autoimmune diseases. A method which reduces the destruction of targeted tissues that is initiated by autoreactive T cells is especially desirable.

SUMMARY OF THE INVENTION

The present invention provides methods for blocking or reducing autoreactive T cell-initiated destruction of tissues in a mammal. The methods employ an agent that inhibits or reduces interaction of the CD24 polypeptide with its functional ligand. The CD24 polypeptide is found on the cell membrane of activated T cells and other cell types, such as B cells, dendritic cells, epithelial cells and vascular endothelial cells.

In one embodiment, the method comprises administering a pharmaceutical composition comprising a biologically effective amount of an isolated and purified polypeptide, referred to hereinafter as the "HSA/CD24" polypeptide, a fusion protein comprising the HSA/CD24 polypeptide, or a biologically active fragment of the HSA/CD24 polypeptide to a mammal in need of the same, i.e., a mammal who is suspected of having, known to have, or predisposed to have an autoimmune disease. As used herein, "mammal" refers to rats, mice, cats, dogs, cows, pigs, rabbits, and primates. Exemplary primates include monkeys, chimpanzees, and humans. As used herein the term "HSA/CD24" refers not only to the protein portion of the heat stable antigen (HSA) found on the surface of mouse cells but also to the mammalian homologs of mouse HSA. Thus, the term "HSA/CD24", as used in the present application, encompasses the polypeptide portion of human CD24 and rat CD24, the known human and rat homologs of mouse HSA. Preferably, the HSA/CD24 polypeptide is glycosylated. The fusion protein comprises the HSA/CD24 polypeptide or a truncated form of the HSA/CD24 inked by a peptide bond to a peptide or protein tag. In a preferred embodiment, the HSA/CD24 fragment comprises the core region of the HSA/CD24 polypeptide.

In another embodiment, the method comprises administering a pharmaceutical composition comprising a biologically effective amount of an anti-HSA/CD24 antibody or anti-HSA/CD24 Fab fragments to a mammal known to have, suspected of having, or predisposed to having an autoimmune disease.

In another aspect, the method comprises administering to the subject an agent that reduces expression of the CD24 polypeptide in T cells. Such methods employ agents that disrupt the function of the CD24 gene at the genomic, transcriptional, post-transcriptional and translational levels. In one embodiment, the agent is an antisense molecule (referred to hereinafter as "CD24 antisense") which reduces transcription of the CD24 gene or translation of the CD24 gene transcript in autoreactive T cells. In another embodiment, the agent is a double stranded RNA molecule (referred to hereinafter as "CD24 dsRNAi") which interferes with expression of the CD24 gene.

The present invention also relates to a method of blocking binding of autoreactive T cells to vascular endothelial cells. In one aspect, the method comprises contacting the vascular endothelial cells with a sufficient amount of an HSA/CD24 polypeptide or a fragment thereof, or a fusion protein comprising HSA/CD24 polypeptide or a fragment thereof, or anti-HSA antibodies to inhibit interaction of the autoreactive T cells with the vascular endothelial cells. In another aspect, the method comprises introducing an oligonucleotide or polynucleotide that inhibits expression of the CD24 polypeptide into the autoreactive T cell, or the vascular endothelial cell or both. Examples of such oligonucleotides and polynucleotides include, but are not limited to, a CD24 antisense oligonucleotide, an expression vector comprising a polynucleotide or nucleic acid encoding a CD24 antisense oligonucleotide, a CD24 dsRNAi, and an expression vector comprising a polynucleotide or nucleic acid encoding a CD24 dsRNAi.

The present invention also relates to isolated and purified HSA/CD24 fusion proteins employed in the above-described methods and to transgenic or knock in mice that express the human CD24 protein on their T cells or their vascular endothelial cells or all other cell types that normally express CD24 but, as a result of targeted mutation, do not express murine HSA on any cells. Such mice provide a unique model to test the effectiveness of drugs designed to block or enhance the biological function of human CD24-mediated autoimmune diseases.

BRIEF DESCRIPTION OF THE FIGURES

FIG. 3. Requirement for HSA expression on both T cells and non-T host cells for the induction of EAE. Histology (63× for a, b, c and the left panel of d; 200× for the right panel of d) of spinal cords of the HSA(−/−)(a, b) or WT(c, d) recipient mice on day 12 after adoptive transfer. Draining lymph node cells were isolated from either WT or HSA(/−) mice after immunization, and were stimulated with antigen and IL2 for 4 days in vitro. The activated T cells were injected into either WT or HSA(−/−) mice ($100\times10^6$ cells per mouse). EAE development was monitored daily for clinical signs. At 12 days after transfer, recipient mice were sacrificed and spinal cords were processed for histological examination. No disease was observed in WT>HSA(−/−), HSA(−/−)>WT, or HSA(−/)>HSA(−/−) recipients.

FIG. 7 shows the amino acid sequence, SEQ ID NO. 1, of the mouse HSA polypeptide. The signal peptide extends from amino acid 1 through amino acid 26 of the sequence. The glycophosphatidyl (GPI) anchor region includes and extends from amino acid 54 through amino acid 76.

FIG. 8 shows the amino acid sequence, SEQ ID NO. 2, of the human CD24 polypeptide. The signal peptide extends from amino acid 1 through amino acid 26 of the sequence. The glycophosphatidyl (GPI) anchor region includes and extends from amino acid 60 through amino acid 80.

FIG. 9 shows the amino acid sequence, SEQ ID NO. 3, of the rat CD24 polypeptide. The signal peptide extends from amino acid 1 through amino acid 26 of the sequence. The glycophosphatidyl (GPI) anchor region includes and extends from amino acid 57 through amino acid 76.

FIG. 10 shows the DNA sequence, SEQ ID NO. 4, of a fusion gene which comprises a nucleotide sequence encoding HSA fused to the genomic sequence of human IgG1 Fc. The predicted sequence of the cDNA, SEQ ID NO. 5, which results from splicing of the introns IgG1 Fc sequence and the predicted amino acid sequence, SEQ ID NO. 14, are also shown in this figure. The normal font with under line is HSA sequence, bold phase is new sequence, italics is IgG1 Fc sequence.

FIG. 14 shows a comparison of mouse and human CD24 cDNA sequences, and the preferred sequences to be targeted by CD24 antisense RNA and CD24 dsRNAi. Human CD24 and mouse CD24 cDNA sequences (Human CD24 (XM_099027) and Mouse CD24 (NM_009846)) are aligned by double blast search. The regions with a stretch of identity that are 17 or more base pairs in length are highlighted as preferred targets for CD24 antisense and dsRNAi agents (SEQ ID NOS 24-29, respectively, in order of appearance).

DETAILED DESCRIPTION OF THE INVENTION

Figure 1C:
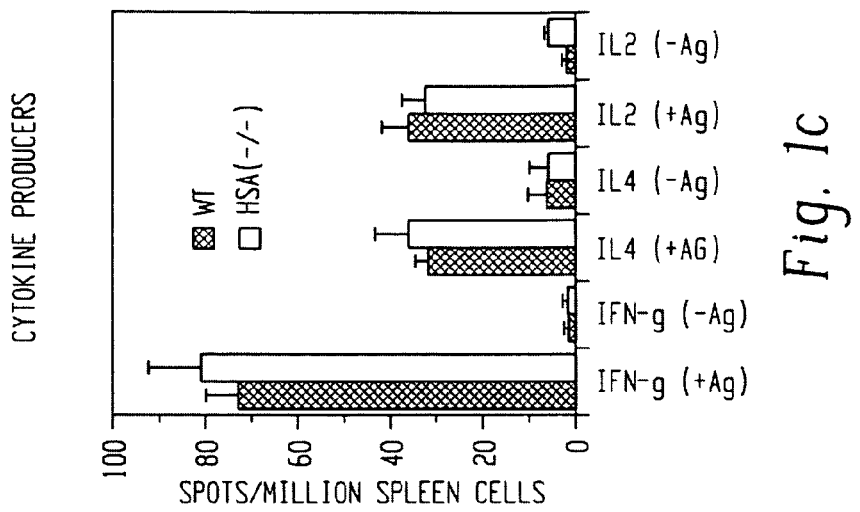
FIG. 1. Targeted mutations of HSA and CD28 reveal two distinct checkpoints in the development of EAE. a. Targeted mutations of either HSA or CD28 prevent induction of EAE. WT, CD28(−/−) or HSA(−/−) mice were immunized with MOG peptide. Clinical signs were scored as described in the method section. b. Proliferative response of lymph node T cells to MOG peptides. Draining lymph node cells from day 10-immunized mice were stimulated with given concentrations of MOG peptide and irradiated syngeneic naive spleen cells as antigen-presenting cells. c. Enumeration of cytokine-producers by ELISpot. Draining lymph node cells used in b were used as responder cells. The numbers of cells secreting either IL2, IL4, and IFNγ among $1\times10^6$ lymph node cells in response to MOG peptide (AA35-55) were presented. Data shown were means+/−SEM from three independent experiments.

The present invention provides methods for blocking destruction of tissue by autoreactive T cells in a mammalian subject. The methods employ agents which inhibit or reduce, either directly or indirectly, the interaction of the CD24 polypeptide with its functional ligand. The CD 24 polypeptide is present on the cell membrane of activated T cells and other cell types such as B cells, dendritic cells, epithelial cells and vascular endothelial cells.

In one embodiment, the method comprises administering a pharmaceutical composition comprising a biologically effective amount of an isolated and purified HSA/CD24 polypeptide or a fragment thereof to a mammal suspected of having an autoimmune disease. In another embodiment a fusion protein comprising the HSA/CD24 polypeptide or fragment thereof linked by a peptide bond to a peptide or protein tag is administered to the mammal. Preferably, the HSA/CD24 polypeptide is glycosylated. In another embodiment an antibody which is immunospecific for the HSA/CD24 polypeptide is administered to the mammal.

In another aspect, the method comprises administering to the subject an agent that reduces expression of the CD24 polypeptide in T cells. Such methods employ agents that disrupt the function of the CD24 gene at the genomic, transcriptional, post-transcriptional and translational levels. In this aspect, embodiments of the present method employ antisense molecules or dsRNAi to inhibit expression of the CD24/HSA gene and production of the CD24 polypeptide in the autoreactive T cells of the mammalian subject.

The present invention also relates to a method of treating a human subject known to have, suspected of having, or predisposed to having an autoimmune disease. The methods involve treating the human subject with an agent which inhibit or reduce, either directly or indirectly, the interaction of the CD24 polypeptide which is present on the cell surface of the subject's cells, including but not limited to activated T cells, with the functional ligand of CD24. In accordance with the present invention, it is believed that such ligands include, but are not limited to, CD24 itself, P-selectin, and very late antigen 4.

In one aspect, the therapeutic method comprises administering a pharmaceutical composition comprising a biologically effective amount of an isolated and purified human CD24 polypeptide or fragment thereof, or a fusion protein comprising such molecule, to the human subject. In another embodiment of this therapeutic method, the pharmaceutical composition comprises anti-human CD24 antibodies or their Fab fragments. Preferably, the anti-human CD24 antibody is a monoclonal antibody, more preferably a humanized monoclonal anti-human CD24 antibody. Preferably, the pharmaceutical composition is administered after autoreactive T cells have been detected in the human subject.

Preferably, the pharmaceutical composition is administered by injection. The present method is useful for treating subjects suspected of having autoimmune diseases such as for example, multiple sclerosis (MS), rheumatoid arthritis, and insulin-dependent diabetes mellitus. By "treating" is meant ameliorating or tempering the severity of the condition, either occurring or expected to occur in the future. In cases of autoimmune demyelinating diseases of the CNS such as for example MS, the pharmaceutical composition is administered either when patients have clinical symptoms, or when they are in temporary remission. Preferably, the protocol involves intravenous injection. In the case of rheumatoid arthritis, the pharmaceutical composition, preferably, is administered intravenously (i.v.) after the acute symptoms are relieved by other therapeutic methods. In the case of insulin dependent diabetes mellitus, the pharmaceutical composition, preferably, is administered intravenously after autoreactive T cells are detected in the peripheral blood.

Further embodiments of this therapeutic method employ antisense molecules or dsRNAi to inhibit expression of the CD24 gene and production of CD24 polypeptide in the T cells of the human subject.

Pharmaceutical Composition

The pharmaceutical composition comprises a biologically effective amount of an HSA/CD24 polypeptide or a biologically active variant thereof or alternatively a fragment of an HSA/CD24 polypeptide or a biologically active variant thereof, and preferably a relatively inert topical carrier. Many such carriers are routinely used and can be identified by reference to pharmaceutical texts.

HSA Antigen

The mouse HSA antigen and the mammalian homologs thereof are polypeptides comprising approximately 76-80 amino acids. The HSA polypeptide and the mammalian homologs thereof are cell surface molecules which are linked to the cell membrane via a glycophosphatidylinositol (GPI) tail. The HSA antigen is constitutively expressed on most hematopoietic and developing neuronal cells. In some lymphocytes, such as for example T cells, expression of the HSA polypeptide is induced. As shown in FIGS. 7-9, the immature forms of mouse HSA antigen, human CD24 and rat CD24 comprise a signal sequence, a core region that is maintained in the mature protein, and a GPI anchor region. As shown in FIG. 7, the signal sequence of the mouse HSA antigen includes amino acid 1 through amino acid 26 of SEQ ID NO. 1; the core region includes amino acid 27 through amino acid 53 of SEQ ID NO. 1; and the GPI region includes amino acid 54 through amino acid 75 of SEQ ID NO. 1. As shown in FIG. 8, the signal sequence of the human CD24 antigen includes amino acid 1 through amino acid 26 of SEQ ID NO.2; the core region includes amino acid 27 through amino acid 57 of SEQ ID NO. 2 and the GPI region includes amino acid 58 through amino acid 80 of SEQ ID NO. 2. As shown in FIG. 9, the signal sequence of the rat CD24 antigen includes amino acid 1 through amino acid 26 of SEQ ID NO.3; the core region includes amino acid 27 through amino acid 56 of SEQ ID NO. 3 and the GPI region includes amino acid 57 through amino acid 76 of SEQ ID NO. 3. The nucleotide sequence of a polynucleotide which encodes the human CD4 polypeptide is available at the GenBank Accession No. AK000168. The nucleotide sequence of a cDNA which encodes the rat CD24 polypeptide is available at GenBank Accession No. AWK12164. The nucleotide sequence of a cDNA which encodes mouse HSA antigen is available at GenBank Accession M58661.

The present invention relates to novel method of using an HSA/CD24 polypeptide or fragment thereof to treat autoimmune diseases. Preferably, the polypeptide or fragment is glycosylated. In one embodiment the HSA/CD24 fragment is a truncated form of the HSA/CD24 polypeptide which lacks a few amino acids, i.e., from 1 to 2 amino acids, at the amino terminus or carboxy terminus thereof. In another embodiment the HSA/CD24 fragment is a polypeptide which comprises essentially only the core region of the HSA/CD24 polypeptide, i.e. the HSA/CD24 fragment lacks most or all of the signal peptide and most or all of the CPI anchor region. As used herein the term HSA/CD24 polypeptide comprises all mammalian homologs of mouse HSA, including human CD24 and rat CD24.

The HSA/CD24 polypeptide or HSA/CD24 fragment that is used in the pharmaceutical composition is the naturally-occurring HSA/CD24 polypeptide, a biologically active fragment of the naturally-occurring HSA/CD24 polypeptide, a biologically active variant of the naturally-occurring HSA/CD24 polypeptide, or a biologically active variant of a fragment of the naturally-occurring HSA/CD24 polypeptide The biologically active variant of the HSA/CD24 polypeptide has an amino acid sequence which is at least 80%, more preferably at least 93%, most preferably at least 96% identical to the amino acid sequence of the naturally occurring HSA/CD24 polypeptide that is present in the mammal to whom the pharmaceutical composition is being administered. Similarly, the biologically active variant of the fragment of the HSA/CD24 polypeptide has an amino acid sequence which is at least 80%, preferably at least 90%, more preferably at least 95% identical to the amino acid sequence of the corresponding naturally-occurring HSA/CD24 fragment. For murine HSA, alteration in Positions 1(Asn), 4(Ser), 13(Asn), 15(Ser), 17(Ser), 21(Ser), 22(Asn), 24(Thr) and 25(Thr) of the mature peptide, i.e., the peptide which lacks the signal peptide, may alter glycosylation and interfere with its ability to block destruction of tissue by autoreactive T cells. Thus, it is preferred that alternations not be made at these sites. In the human homologue of HSA, i.e., human CD24, 20 out of 31 amino acids are potential glycosylation sites.

An HSA/CD24 polypeptide which is less than 100% identical to the naturally occurring HSA/CD24 polypeptide has an altered sequence in which one or more of the amino acids in the HSA homologue is deleted or substituted, or one or more amino acids are inserted into the sequence of the naturally occurring HSA/CD24 polypeptide. HSA/CD24 sequences which are at least 95% identical to the naturally occurring HSA/CD24 sequence have no more than 5 alterations, i.e., any combination of deletions, insertions or substitutions, per 100 amino acids of the reference sequence. Percent identity is determined by comparing the amino acid sequence of the altered HSA/CD24 sequence with the naturally occurring sequence using MEGALIGN project in the DNA STAR program. Sequences are aligned for identity calculations using the method of the software basic local alignment search tool in the BLAST network service (the National Center for Biotechnology Information, Bethesda, Md.) which employs the method of Altschul, S. F., Gish, W., Miller, W., Myers, E. W. & Lipman, D. J. (1990) *J. Mol. Biol.* 215, 403-410. Identities are calculated by the Align program (DNAstar, Inc.) In all cases, internal gaps and amino acid insertions in the candidate sequence as aligned are not ignored when making the identity calculation.

While it is possible to have nonconservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic, residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

The biologically active fragments and variants of a naturally-occurring HSA/CD24 have an $ID_{50}$ which is comparable to, i.e., not more than twice the value of, the $ID_{50}$ of the corresponding naturally-occurring HSA/CD24 polypeptide. The $ID_{50}$ of the HSA/CD24 variant or fragment and its corresponding naturally-occurring polypeptide is determined by measuring the amount of these polypeptides needed to reduce the clinical symptoms in experimental autoimmune models, such as EAE or Type II diabetes in NOD mouse or rat. Alternatively, one can determine the $ID_{50}$ of the biologically active HSA/CD24 variant or fragment and its corresponding naturally occurring HSA/CD24 polypeptide by an adhesion assay or assays that measure migration of T cells through endothelial cell monolayer in transwell culture. The amount of the biologically active variant of the HSA/CD24 polypeptide or fragment thereof needed to reduce binding of activated T cells to vascular endothelial cells by at least 50%, preferably, is no greater than twice the amount of the corresponding naturally occurring HSA/CD24 polypeptide or fragment thereof.

The present method also employs fusion proteins comprising an HSA/CD24 polypeptide or a biologically active fragment thereof and a tag, i.e., or one or more amino acids, preferably from about 5 to 300 amino acids which are added to the amino terminus of, the carboxy terminus of, or any point within the amino acid sequence of the HSA/CD24 polypeptide or the biologically active fragment thereof. Preferably, the HSA/CD24 polypeptide or core region thereof is glycosylated. Typically, such additions are made to simplify purification of an expressed recombinant form of the corresponding HSA/CD24 polypeptide or core region thereof. Such tags are known in the art. Representative examples of such tags include sequences which encode a series of histidine residues, the epitope tag FLAG, the Herpes simplex glycoprotein D, beta-galactosidase, maltose binding protein, or glutathione S-transferase. Preferably, the fusion protein comprises the HSA polypeptide or a fragment thereof linked by a peptide bond to the hinge-CH2-CH3 regions of human immunoglobin G1 ("IgG1"). The fusion protein can be easily purified by affinity chromatography using either anti-IgG or protein A or protein G. Since IgG is not immunogenic in humans, the fusion protein can be administrated repeatedly if necessary.

Methods of Preparing the HSA/CD24 Polypeptide or Fusion Protein

The HSA/CD24 polypeptides and fusion proteins may be produced by using cell-free translation systems and RNA molecules derived from DNA constructs that encode the polypeptide or fusion protein. Preferably, the HSA/CD24 polypeptide or fusion protein is made by transfecting host cells with expression vectors that comprise a DNA sequence that encodes the respective HSA/CD24 polypeptide or fusion protein and then inducing expression of the polypeptide in the host cells. For recombinant production, recombinant constructs comprising one or more of the sequences which encode the HSA/CD24 polypeptide or fusion protein are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The HSA/CD24 polypeptide or fusion protein may be expressed in suitable host cells, such as for example, mammalian cells, yeast, insect cells or other cells under the control of appropriate promoters using conventional techniques. Suitable hosts include, but are not limited to, CHO, COS cells and 293 HEK cells. Following transformation of the suitable host strain and growth of the host strain to an appropriate cell density, the cells are harvested by centrifugation, disrupted by physical or chemical means, and the resulting crude extract retained for further purification of the epitope or chimeric peptide. For obtaining properly glycosylated forms of the protein, it is preferred that CHO cells be used.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant polypeptide.

Carrier

The acceptable carrier is a physiologically acceptable diluent or adjuvant. The term physiologically acceptable means a non-toxic material that does not interfere with the effectiveness of HSA. The characteristics of the carrier will depend on the route of administration and particular compound or combination of compounds in the composition. Preparation of such formulations is within the level of skill in the art. The composition may further contain other agents which either enhance the activity of the HSA or complement its activity. The composition may further comprise fillers, salts, buffers, stabilizers, solubilizers, and other materials well known in the art.

Dosage

A biologically effective amount is an amount sufficient to partially or completely block destruction of the targeted tissue initiated by the autoreactive T cell or to ameliorate the pathological effects of the autoimmune disease. The effective amount can be achieved by one administration of the composition. Alternatively, the effective amount is achieved by multiple administration of the composition to the mammal.

Antibodies

The invention further provides a therapeutic method which comprises administering a pharmaceutically effective amount of an anti-HSA/CD24 antibody, preferably a humanized anti-HSA/CD24 antibody, to a human subject suspected of having an autoimmune disease. The anti-HSA/CD24 antibody is immunospecific for the HSA/CD24 polypeptide meaning the antibody has substantially greater affinity for the HSA/CD24 polypeptide than for other polypeptides that are found on the T cells of the mammal being treated. Various forms of an anti-HSA/CD24 antibody may be used in this therapeutic method. For example, the anti-HSA/CD24 antibody may be a full length antibody (e.g., having a human immunoglobulin constant region) or an antibody fragment (e.g. a F(ab')$_2$).

The term "antibody" as used herein encompasses monoclonal antibodies (including full length monoclonal antibodies), polyclonal antibodies, multispecific antibodies (e.g., bispecific antibodies), and antibody fragments so long as they exhibit the desired biological activity. "Antibody fragments" comprise a portion of a full length antibody, generally the antigen binding or variable region thereof. Examples of antibody fragments include Fab, Fab', F(ab')$_2$, and Fv fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

In order to avoid potential immunogenicity of the mAbs in human, the mAbs that have desired function are preferably humanized. "Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321: 522-525 (1986); Reichmann et al., Nature 332: 323-329 (1988); and Presta, Curr. Op. Struct. Biol. 2: 593-596 (1992).

Alternatively, transgenic mice with human IgV and IgC genes may be used to produce human mAb specific for human CD24. These mice are available from Abgenix, Inc., and Mederex, Inc, and the art has been described fully (Nature Genetics, 1997, 15: 146).

Antisense Molecules

In certain aspects, the present therapeutic methods employ agents which reduce or inhibit expression of the CD24 gene or production of the CD24 polypeptide in the T cells of human subjects known to have or suspected of having an autoimmune disease, such as multiple sclerosis, rheumatoid arthritis, and type II diabetes.

One such agent is an antisense molecule. The antisense molecule for CD24 is an oligomer which comprises from 20 to 200 bases, preferably less than 100 bases, and is targeted to a nucleic acid encoding the human CD24 polypeptide, in other words, the human CD24 gene or mRNA expressed from the human CD24 gene. The targeting process involves determination of a site or sites within the nucleic acid sequence of the CD24 gene or mRNA for the oligonucleotide interaction to occur such that transcription of the CD24 gene or translation of the CD24 mRNA will be reduced in the human subject's T cells. Once the target site or sites have been identified, oligonucleotides are chosen which are sufficiently complementary to the target, i.e., hybridize sufficiently well and with sufficient specificity, to give the desired reduction in expression of the CD24 polypeptide. Such inhibition can be measured in ways which are routine in the art, for example by Northern blot assay of mRNA expression or Western blot assay of protein expression, or flow cytometry analysis for cell surface expression.

"Hybridization", as used herein means hydrogen bonding, also known as Watson-Crick base pairing, between complementary bases, usually on opposite nucleic acid strands or two regions of a nucleic acid strand. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted. Affinity of an oligonucleotide for its target (in this case a nucleic acid encoding CD24 polypeptide) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target.

In the context of this therapeutic method, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Modifications may be on one or more bases, sugars, or backbone linkages, or combinations of these; such modifications are well known in the art. Modified or substituted oligonucleotides are often preferred over native forms because of properties such as, for example, enhanced cellular uptake and increased stability in the presence of nucleases. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. In some cases, oligonucleotide modifications which enhance target binding affinity are also, independently, able to enhance nuclease resistance. A discussion of antisense oligonucleotides and some desirable modifications can be found in De Mesmaeker et al. Acc. Chem. Res. 1995, 28, 366-374.

Specific examples of some oligonucleotides contemplated for the present method include those containing modified backbones, for example, phosphorothioates, phosphotriesters, methyl phosphonates, short chain alkyl or cycloalkyl intersugar linkages or short chain heteroatomic or heterocyclic intersugar linkages. The oligonucleotides may be chimeric oligonucleotides. "Chimeric oligonucleotides" as used herein mean oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for RNase H cleavage. In one embodiment, a chimeric oligonucleotide comprises at least one region modified to increase target binding affinity, and, usually, a region that acts as a substrate for RNAse H. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis.

Alternatively, an expression vector comprising a polynucleotide or nucleic acid encoding an antisense oligonucleotide targeted to nucleic acids that encode the CD24 polypeptide are introduced into the subject's T cells. The CD24 antisense encoding nucleic acid is operatively linked to a promoter. A "promoter" is a sequence that directs the binding of RNA polymerase and thereby promotes RNA synthesis, which in the present method is synthesis of the antisense oligonucleotide. Operatively linked is understood to mean that the CD24 antisense encoding sequence is joined to the promoter region such that the promoter is oriented 5' to the CD24 antisense encoding sequence and is of an appropriate distance from the transcription start site, so that the transcription of the polynucleotide which encodes the CD24 antisense oligonucleotide will be dependent on or controlled by the promoter sequence. The arts of restriction enzyme digestion and nucleic acid ligation to be used in construction of the CD24 antisense encoding polynucleotide-promoter construct are well known in the art as exemplified by Maniatis et al., Molecular Cloning, A Laboratory Manual, Cold Spring Harbor, N.Y., 1982, (incorporated herein by reference). Many examples of constitutive promoters have been described in the art such as those isolated from cytomegalovirus early gene, murine MHC class I, actin, etc. An example of T-cell specific promoter is the lck promoter (EMBO J. 9: 3821-3829, 1990), which we have shown to be able to drive T cell-specific expression (Eur. J. Immunol 27:2524-2528, 1997). An example of vascular cell specific vector is described by Sato et al. (Proc. Natl. Acad Sci USA, 94:3058-63(1997)

dsRNAi

Another agent for reducing or inhibiting expression of the CD24 gene and production of the polypeptide in the T cells of human subjects is a double stranded oligonucleotide or polynucleotide known as dsRNAi. One strand of the dsRNA comprises a CD24 sense sequence; while the other strand comprises a CD24 antisense sequence. Preferably, the dsRNAi further comprises a linker connecting the antisense sequence to the sense sequence. Preferably, the CD24 sense and antisense sequences are from 19-30 bases in length. The linker is at least 10 bases in length, and preferably, from 10-20 bases in length. The CD24 dsRNAi prevents accumulation of CD24 mRNA in the transformed cells, most likely through a post-transcription gene silencing method known in the art as double-stranded RNA interferences.

dsRNAi can be synthesized using standard techniques. For example single-stranded RNA corresponding to the sense CD24 sequence, and single stranded RNA corresponding to the antisense CD24 sequence can be synthesized according to methods known in the art. The single stranded RNAs can then be annealed in vitro by methods known in the art, to produce the dsRNA. To increase the stability of the dsRNAi, several nucleotide with de-oxyl-nucleotide can be incorporated at the 3' of the oligonucleotides.

Alternatively, an expression vector comprising a polynucleotide or nucleic acid encoding CD24 dsRNAi is introduced into the subject's T cells or, the subject's vascular endothelial cells, or both. Such polynucleotide comprises a sequence which encodes a sense CD24 RNA coding sequence and an antisense CD24 RNA coding sequence and a linker sequence which links the sense CD24 RNA coding sequence to the antisense CD24 RNA coding sequence. The expression vector further comprises a promoter operatively linked to the CD24 dsRNAi coding sequence.

Targeting of the CD24 Antisense and dsRNAi Molecules

In accordance with the present method, targeted regions of the CD24 gene and CD24 mRNA include not only the coding region for the CD24 polypeptide, but also the 5'-untranslated region, the 3'-untranslated region, the 5' cap region, intron regions and intron/exon or splice junction regions of the targeted nucleic acid. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the CD24 mRNA function is to cause interference with expression of the CD24 polypeptide.

Although numerous areas can be targeted for anti-sense and dsRNAi molecules, there is a significant advantage to target areas in which the sequence is completely conserved between CD24 in mouse and man. In this way, the CD24 anti-sense and dsRNAi molecules can be screened for both efficacy and toxicity in preclinical models before they are used for human clinical trials. A comparison between human and mouse CD24 cDNA sequence, as listed in FIG. 14, revealed 8 areas within the 2.1 kb areas of human CD24 that can be as targets for antisense and dsRNAi molecules.

Delivery of the CD24 Antisense and dsRNAi Molecules

Single-stranded CD24 anti-sense oligonucleotides and dsRNAi molecules can be introduced into the subject's cells, including but not limited to T cells, vascular endothelial cells, or both. The molecules are introduced into the cells either ex vivo or in vivo. "Ex vivo" means that these molecules are introduced into the T cells or endothelial cells outside the body of the subject from whom the T cells or endothelial cells are obtained. The cells are then re-introduced back into the subject. For in vivo delivery to these target cells, the CD24 antisense and dsRNAi molecules are introduced into the subject by injection. Preferably, the injection is intravenous, or intralesional injection (as in the case of rheumatoid arthritis).

Delivery of the CD24 antisense or CD24 dsRNAi encoding polynucleotide-promoter construct into the subject may be either direct, in which case the subject is directly exposed to the construct or construct-carrying vector, or indirect, in which case cells are first transformed with the construct in vitro, then transplanted into the patient. The latter method is referred to as cell-based gene-therapy.

A retroviral vector may be used to deliver the CD24 antisense and CD24 dsRNAi encoding construct (see Miller et al., 1993, Meth. Enzymol. 217:581-599). Retroviral vectors have been modified to delete retroviral sequences that are not necessary for packaging of the viral genome and are maintained in infected cells by integration into genomic sites upon cell division. More detail about retroviral vectors can be found in Boesen et al. (1994) *Biotherapy* 6:291-302: Clowes et al. (1994) *J. Clin. Invest.* 93:644-651; Kiem et al. (1994) *Blood* 83:1467-1473; Salmons and Gunzberg (1993) *Human Gene Therapy* 4:129-141; and Grossman and Wilson (1993) *Curr. Opin. in Genetics and Devel.* 3:110-114.

A lentiviral vector (Science. 1996 Apr. 12;272(5259):263-7.) can also be used to deliver genes that encode the antisense drug either in vivo or to ex vivo cells. Unlike a typical retroviral vector, the lentiviral vector can be used to deliver gene to non-dividing cells.

Alternatively, liposomes may be employed to deliver the CD24 antisense and dsRNAi encoding constructs to target tissues using methods known in the art. The liposomes may be constructed to contain a targeting moiety or ligand, such as an antigen, an antibody, or a virus on their surface to facilitate delivery to the appropriate tissue. For example, liposomes prepared with ultraviolet (UV) inactivated Hemagglutinating Virus of Japan (HVJ) may be used to deliver DNA to selected tissues (Morishita, et al.). The liposomes may also be surface-coated with phospholipid-polyethyleneglycol conjugates, to extend blood circulation time and allow for greater targeting via the bloodstream. Liposomes of this type are well known. A variety of liposome have been described in the art to deliver double-stranded nucleotide or naked DNA into cells, both for ex vivo cells, or for in vivo delivery.

Receptor-mediated endocytic pathways for the uptake of DNA may permit the targeted delivery of the CD24 antisense and dsRNAi encoding constructs to specific cell types in vivo. Receptor-mediated methods of polynucleotide delivery in vivo involve the generation of complexes between vectors and specific polypeptide ligands that can be recognized by receptors on the cell surface.

For general reviews of the methods of in vivo polynucleotide delivery (also referred to as gene therapy), see Goldspiel et al (1993) *Clinical Pharmacy* 12:488-505; Wu and Wu (1991) *Biotherapy* 3:87-95; Tolstoshev (1993) *Ann. Rev. Pharmacol. Toxicol.* 32:573-596; Mulligan, (1993) *Science* 260:926-932; and Morgan and Anderson (1993) *Ann. Rev. Biochem.* 62:191-217; May, 1993, TIBTECH 11 (5):155-215. Methods commonly known in the art of recombinant DNA technology which can be used are described in Ausubel et al. (eds.) (1993) *Current Protocols in Molecular Biology*, John Wiley & Sons, NY; and Kriegler (1990) *Gene Transfer and Expression*, A Laboratory Manual, Stockton Press, NY.

Transgenic and Knock-in Mouse Models to Test the Effect of CD24 Blockers In Vivo Since the major cell type in the CNS that expresses HSA is the brain vascular endothelial cells, transgenic vectors that give specific expression of human CD24 in both T cells and vascular endothelial cells are used to prepare the transgenic mice. In one preferred embodiment T cell-specific expression is achieved using a transgenic vector comprised of human CD24 open reading frame and the proximal lck promoter and vascular endothelial cell specific expression is achieved using a transgenic vector comprised of human CD24 open-reading frame and the Tie II promoter, as described in Proc. Natl. Acad Sci USA, 94:3058-63(1997). To avoid interference by the endogenous HSA, the transgenic vector is injected into the fertilized embryos from mice with a targeted mutation of mouse CD24 as described in J. Exp. Med. 185: 251-262, 1997. Alternatively, the transgenic mice expressing the CD24 gene can be bred to the CD24 (−/−) mice to avoid expression of endogenous CD24. The tissue specificity of the transgene expression is verified with anti-CD24 mAb, which is available from Pharmingen (San Diego, Calif.), by flow cytometry and immunhistochemistry according to established procedure.

Alternatively, human CD24 knock-in mice can be developed to screen for therapeutic agents targeted at the human CD24 antigen. The major advantage of the knock-in mice is that all the cells that express murine CD24 can be rendered to express human CD24 genes, and as such, the knock-in mice are more relevant for testing the efficacy and safety of drugs targeted at the human CD24 antigens. Since mouse and human CD24 protein have identical amino acid sequence in the signal peptide region (encoded) regions, the CD24 knock-in mouse can be made by replacing only the coding region in exon 2. Moreover, since a major portion of the coding region encodes for GPI-cleavage signal peptide that will be removed from the mature protein, replacement of the mouse HSA/CD24 with human CD24 can be achieved simply by replacing the 81 bp region that encode for the core region of mature mouse CD24 protein with a 96 bp region that encodes for the core region of mature human CD24 protein. Replacement of some human CD24 protein amino acids with murine counterpart may be tolerated if such replacement does not change the binding activity of these molecules to anti-human CD24 antibodies, and functional ligands of human CD24 protein. For convenience of cloning, the replacement can be significantly larger than proposed region. Once the construct is produced, it is used to transfect mouse embryonic stem (ES) cells, to select for transfectants in which at least one allele of the CD24 gene is replaced the construct through homologous recombination. The recombinant alleles can be screened by PCR and/or Southern blot according the established procedures. The recombinant ES cells are tested for functionality of the recombinant allele. Once this is verified, the ES cells are used to produce chimera mice. Further breeding yield mice that are homozygous for the knock-in alleles, which express human CD24 gene on cells that had been programmed to express CD24.

The transgenic and knock-in mice produced as described above are used to screen drugs targeted at the human CD24 molecules. One example is to screen for drugs which inhibit or ameliorate autoimmune conditions such as multiple sclerosis and diabetes. The most suitable murine model for multiple sclerosis is EAE, which is induced by immunizing mice with MOG according to a established procedure.

The preferred method for testing drugs targeted at CD24 for diabetes is to breed the human CD24 transgenic mice with non-obese diabetic (NOD) mice to cross the transgene to NOD background. The drugs targeted at HSA or its homologue are administrated at approximately 2-3 weeks to determine their ID50 in the reduction of insulitis and spontaneous diabetes.

Blocking Binding of Autoreactive T Cells to Endotheial Cells In Vitro or In Vivo The present invention also relates to a method of blocking binding of autoreactive T cells to endothelial cells, in vitro or in vivo. In one aspect, the method comprises contacting the endothelial cells with a sufficient amount of HSA or a fusion protein comprising HSA to inhibit interaction of the autoreactive T cells with HSA molecules present on the surface of the endothelial cells. The cells may be in vitro, i.e., in tissue culture, or in vivo, i.e., in the body of a mammal. Blocking interaction between the endothelial and T cells in vitro is achieved by adding the protein to a chamber that contains both T cells and endothelial cells. The amount of T cells bound to a monolayer of endothelial cells in the presence or absence of HSA protein is quantified either by counting the number of cells attached, or by other methods to quantify the number of T cells that were labeled prior to adding to the monolayer.

Interaction between the endothelial and autoreactive T cells in vivo is inhibited by injecting the protein intravenously. To quantify the extent of inhibition fluorescent labeled T cells are administered to an animal and the rolling of T cells along the blood vessel is measured using established procedures known in the art.

In another aspect, interaction of autoreactive T cells with vascular endothelial cells is blocked or reduced by inhibiting or reducing expression of the CD24 polypeptide in the autoreactive T cells, the endothelial cells or both. Expression of the CD 24 polypeptide in the target cells is accomplished by introducing CD24 antisense oligonucleotides or CD24 dsRNAi into the target cells, or alternatively, transfecting these cells with a polynucleotide which encodes the CD24 antisense oligonucleotide or CD24 dsRNAi. As used herein, transfect, refers to introduction of a polynucleotide into the cell where the polynucleotide may be incorporated into the genome of the cell, converted into an autonomous replicon, or transiently expressed. The transfection can be in vivo or ex vivo. "Ex vivo transfection" means that transfection occurs outside the body of the subject from whom the target cells were obtained. "In vivo transfection" means transfection of the target cells within the body of the subject.

All references cited herein are specifically incorporated herein in their entirety.

EXAMPLES

The following examples are for illustration only and are not intended to limit the scope of the invention.

Example 1

Treatment of Animals with Experimental Autoimmune Encephalomyelitis with HSAIg

Methods

Mice Wild type C57BL/6 mice (WT) were purchased from the National Cancer Institute (Bethesda, Md.). Mice homozygous for the disrupted HSA (produced with ES cells from C57BL/6 mice) (18) (24) or CD28 (25) (backcrossed to C57BL/6 for more than 8 generations) locus have been described before and are maintained at the animal facilities of the Ohio State University Medical Center. HSA transgenic mice (HSATG) have been described previously (See Zhou, Q., Wu, Y., Nielsen, P. J., and Liu, Y. 1997. Homotypic interaction of the heat-stable antigen is not responsible for its co-stimulatory activity for T cell clonal expansion. *Eur J.*

Immunol. 27: 2524-2528, which is specifically incorporated herein by reference.) and have been backcrossed to C57BL/6j background for more than 5 generations. Mice with HSA exclusively expressed on the T cell lineage (HSATG/HSA (−/−)) were generated by crossing HSATG with the HSA(−/−) mice.

Induction and clinical evaluation of EAE The immunogen, MOG peptide 35-55 of rat origin (MEVGWYRSPFSRVVH-LYRNGK; SEQ ID NO: 13), was synthesized by Research Genetics, Inc. (Huntsville, Ala., USA). The purity of the peptide was >90%. Mice of 8-12 wks of age were immunized subcutaneously with 200 μg MOG peptide in complete Freund's Adjuvant (400 μg of *Mycobacterium tuberculosis* per ml) in a total volume of 100 μl. They received 200 μg of Pertussis toxin (List Biological, Campbell, Calif.) in 200 λl PBS in the tail vein immediately after the immunization, and again 48 hours later. The mice were observed every other day and scored on a scale of 0-5 with gradations of 0.5 for intermediate scores: 0, no clinical signs; 1, loss of tail tone; 2, wobbly gait; 3, hind limb paralysis; 4, hind and fore limb paralysis; 5, death.

T cell proliferation assay Draining lymph node cells were isolated 10 days after immunization. $5 \times 10^5$ cells/well were stimulated with given concentrations of MOG peptide in the presence $6 \times 10^5$ cells/well of irradiated (2,000 rad) syngeneic splenocytes for 60 hours. The cultures were pulsed with $^3$H-thymidine (1 μCi/well; ICN Pharmaceuticals Inc., Costa Mesa, Calif. USA) for another 12 hours, and incorporation of 3H-thymidine was measured in a liquid scintillation P-plate counter.

ELISpot assay to evaluate frequencies of T cells that produce IFN-γ, IL-2 and IL-4 upon restimulation with MOG peptide in vitro The antibody pairs and the procedures have been described (20), except that the MOG peptide was used for stimulation at 10 μg/ml. The numbers presented are those of cytokine producers per million of draining lymph node cells.

Histology

Mice were sacrificed by $CO_2$ inhalation. Spinal cords were removed by insufflation and fixed in 10% formalin/PBS. Paraffin sections were prepared and stained with hematoxylin and eosin. Neurological lesions were graded on each of the 10 cross sections per spinal cord, according the following criteria: 0, no infiltrate; 1, 3 or less focal meningeal infiltrates; 2, more than 3 focal meningeal infiltrates; 3, up to 5 perivascular infiltrate foci in the parenchyma with involvement of less than 5% of the white matter; 4, 5-10 perivascular foci in the parenchyma or invasions involving 5-25% the white matter; 5, more than 10 perivascular foci or diffuse infiltration involving more than 25% of the white matter.

Passive Transfer of EAE

Groups of 8-10 WT and HSA(−/−) mice were immunized with 200 μg of MOG peptide subcutaneously. At 10 days after immunization, draining lymph nodes were harvested and stimulated at $4 \times 10^6$/ml in Click's EHAA medium supplemented. with 15% fetal calf sera, 5% IL-2 supernatant, and 50 μg/ml of MOG peptide for 4 days. $1 \times 10^8$ cells were injected i.p. into each recipient mouse that had been γ-irradiated (550 rad) 1 h earlier.

Preparation of Fusion Protein and Treatment of EAE z

The HSA fragment encoding the signal peptide and the mature protein sequence were amplified by PCR, using GGA AAG CTT ATG GGC AGA GC, SEQ ID NO.:6, as forward primer, CGA GAT CTC TGG TGG TAG CG , SEQ ID NO.:7, as reverse primer, and HSA cDNA as template. The PCR products were digested with Hind III and Bgi II enzymes and were ligated to Hind III and Xba I-digested pCDM8 vector (Invitrogen, San Diego) and a Xba I and Bam HI-treated DNA fragment encoding human IgG1 Fc, which were amplified by PCR using CAG GGA TCC CGA GGG TGA GTA CTA AGC TAG CTT CAG CGC TCC TGC CTG, SEQ ID NO.:15, as forward primer and CTT CGA CCA GTC TAG AAG CAT CCT CGT GCG ACC GCG AGA GC, SEQ ID NO.:8, as reverse primer, and DNA from human peripheral blood as template. The construct was verified by DNA sequencing and was used to transfect the Chinese Hamster Ovary cell line. The cells that secreted HSAIg fusion protein were amplified in DMEM containing 5% fetal calf serum until confluence. The cell monolayers were washed with serum-free medium and cultured in optimal M medium for 72 hours. The supernatants were collected and the HSAIg was purified using a protein G column according to the manufacturer's protocol. The purity of the protein was verified by SDS PAGE.

Results

Figure 1B:
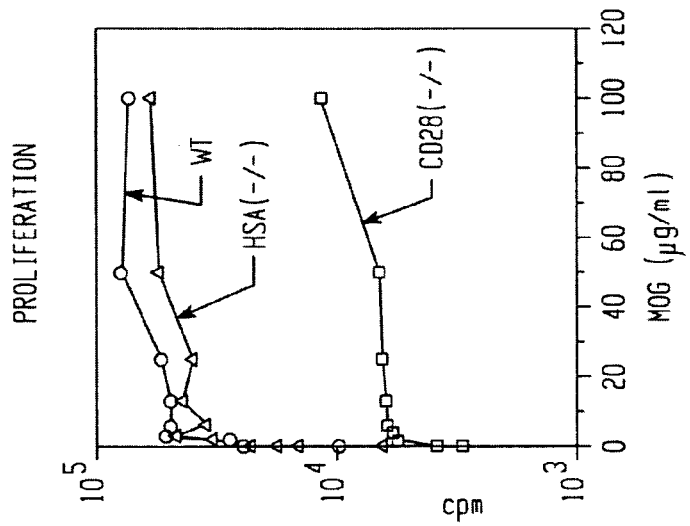
Figure 1A:
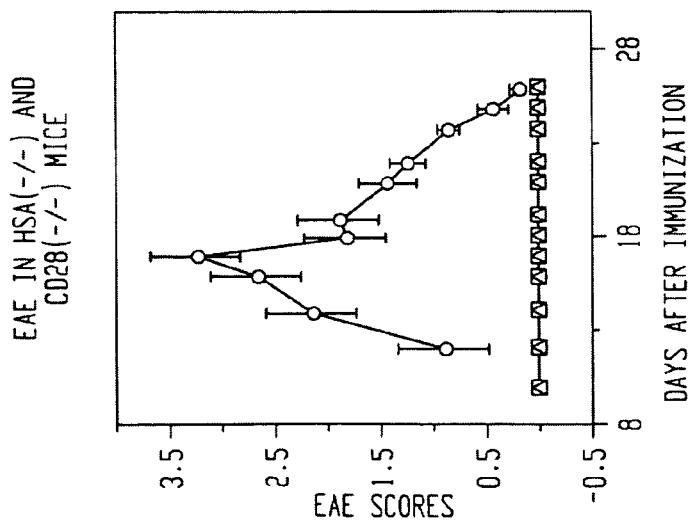

To test if HSA is essential for the development of EAE, we immunized C57BL/6 wild-type (WT), and HSA- or CD28-deficient mice with myelin oligodendrocyte glycoprotein (MOG) peptide AA35-55 in conjunction with complete Freund's adjuvant and pertusis toxin. As shown in FIG. 1a, wild-type mice developed acute EAE within two weeks of peptide immunization, while those with targeted mutation of either HSA or CD28 were completely resistant to EAE induction. Interestingly, while targeted mutation of CD28 ablated induction of MOG-specific T cells, as revealed by proliferative response of draining lymph node cells, that of HSA had little effect on peptide-specific T cell proliferation (FIG. 1b). Moreover, the frequencies of antigen-specific, IL2-, IL4-, and IFNγ-producing cells were not altered in HSA(−/−) mice (FIG. 1c). The anti-MOG peptide IgG responses were also detected in HSA-deficient mice (data not shown). The differential effects of HSA and CD28 mutations on T cell priming reveal that these genes mediate two distinct checkpoints in the development of EAE: CD28 controls induction of auto-reactive T cells, while HSA determines their pathogenicity.

Figures 2A, 2B:
FIG. 2. Histological analysis of spinal cord of MOG immunized WT or HSA(−/−) mice. a: The means and SEM of histological scores of WT and HSA(−/−) mice spinal cords. Ten independent cross sections, from cervical to sacral regions, were examined in each spinal cord. The data are summarized from 30 spinal cord sections from 3 mice in each group. b. Representative histology in immunized WT mice, all sections examined contain histology lesions. c and d. Histology sections (100×) of immunized HSA(−/−) mice. A lesion-free section is presented in c, while a lesion containing section is presented in d.
Figure 2C:
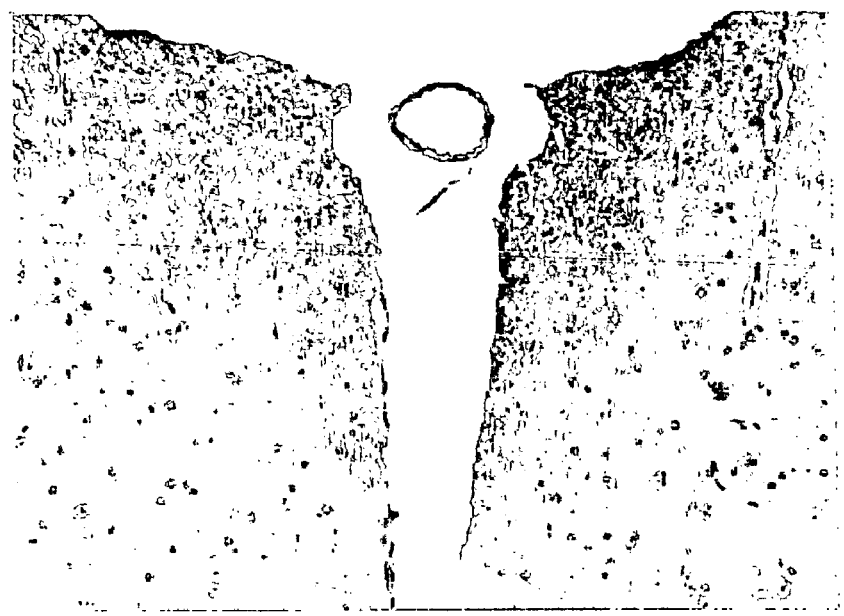
Figure 2D:

Histological analysis of MOG-peptide immunized WT and HSA-confirms the clinical scores. The histological scores were summarized in FIG. 2a, while representative histology sections were presented FIG. 2b-d. As shown in FIG. 2b, active immunization with MOG peptide induces multiple neurological lesions in the wild-type mice, characterized by multiple lesions with extensive invasion of parenchyma. In contrast, the spinal cords of HSA-KO mice are either devoid of any lesion (FIG. 2c), or with one or two low grade lesions involving meninges (FIG. 2d).

Figure 4:
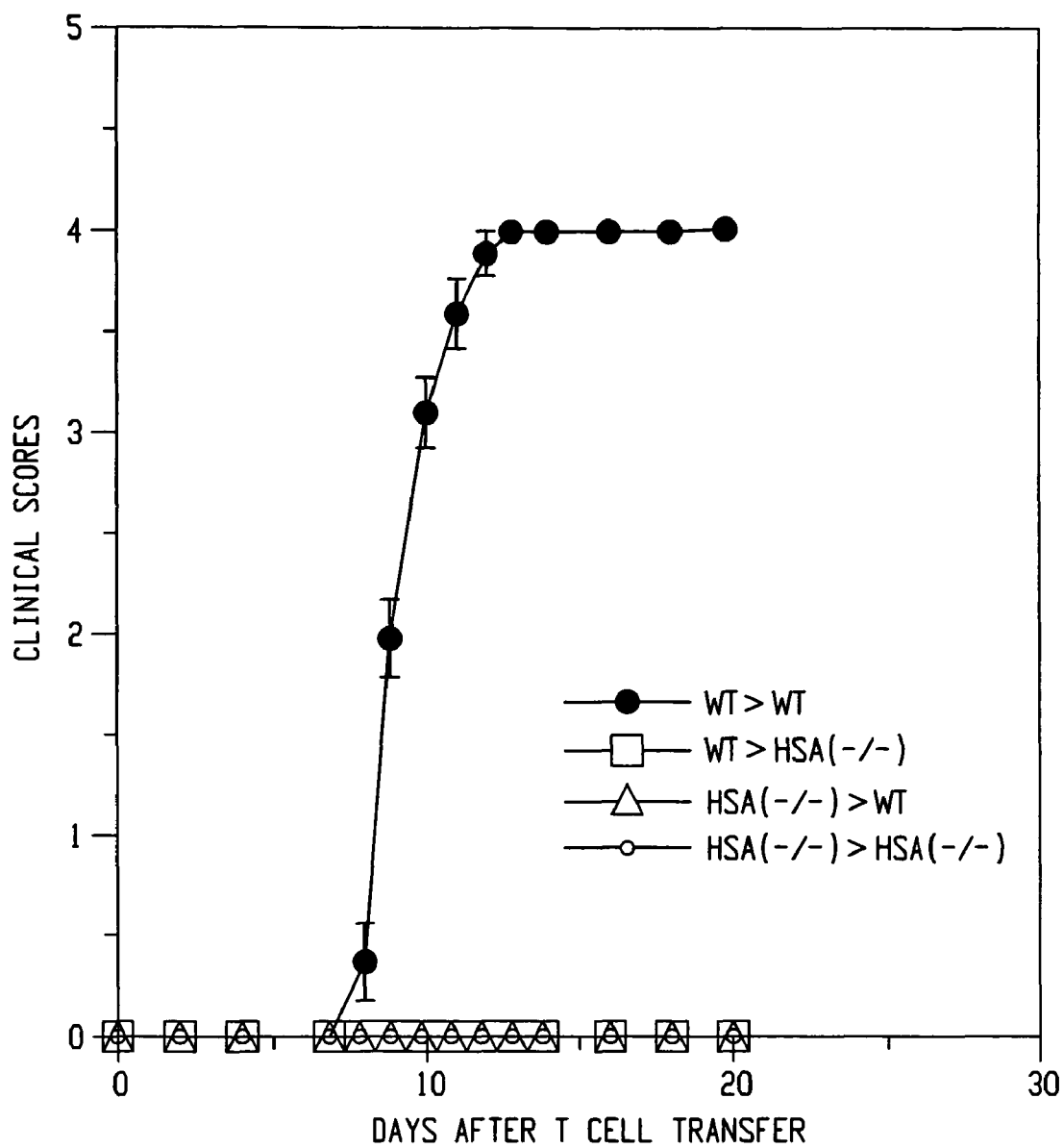
FIG. 4. Clinical scores of the adoptive transfer experiment with 4 (WT>HSA(−/−) and HSA(−/−)>WT groups) or 5 (WT>WT and HSA(−/−)>HSA(−/−) groups) mice per group.

We adoptively transferred activated draining lymph node cells to WT and HSA-deficient recipients. As shown in FIGS. 3 and 4, WT T cells induced severe EAE in WT recipients within 8 days of adoptive transfer. Interestingly, none of the HSA-deficient recipients developed EAE. Thus HSA expression on T cells alone appears insufficient for EAE development. Moreover, T cells from HSA-deficient mice failed to induce disease regardless of HSA gene status in the recipient, which indicates that HSA expression on T cells is necessary for EAE development. These results strongly suggest that HSA must be expressed on both host cells and auto-reactive T cells in order to induce EAE.

To substantiate these observations, we produced mice that expressed HSA exclusively on T cells. We have previously reported the transgenic mice in which expression of HSA was under the control of the Ick proximal promoter (HSATG)

Figure 5A:
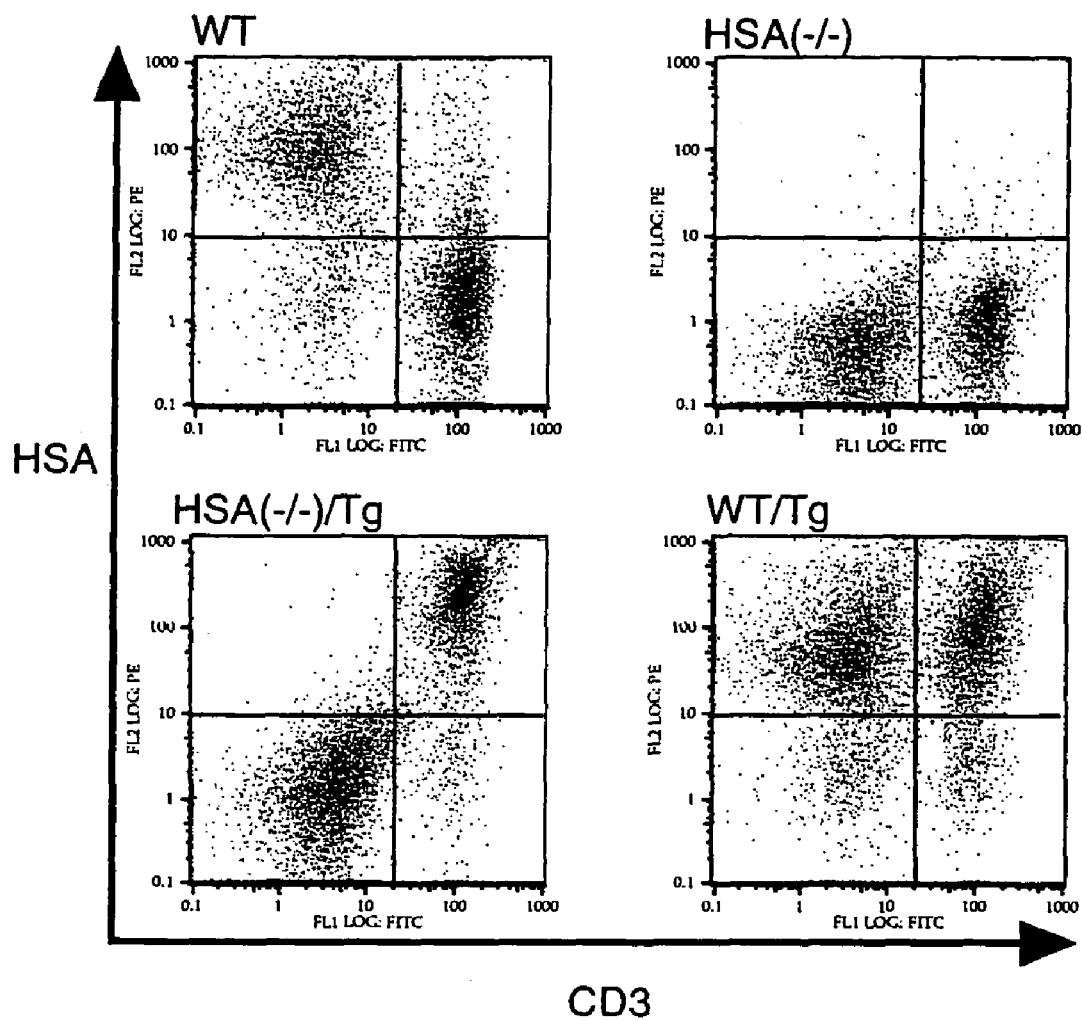
FIG. 5. Transgenic expression of HSA exclusively on T cell lineage is insufficient for EAE development. a. Phenotypes of WT, HSA-TG, HSA(−/−), and HSATG/HSA(−/−) mice by flow cytometry using anti-HSA and anti-CD3 mAbs. b. EAE score in WT, HSATG, HSA(−/−), and HSATG/HSA(−/−) mice after immunization with the MOG peptides.
Figure 5B:
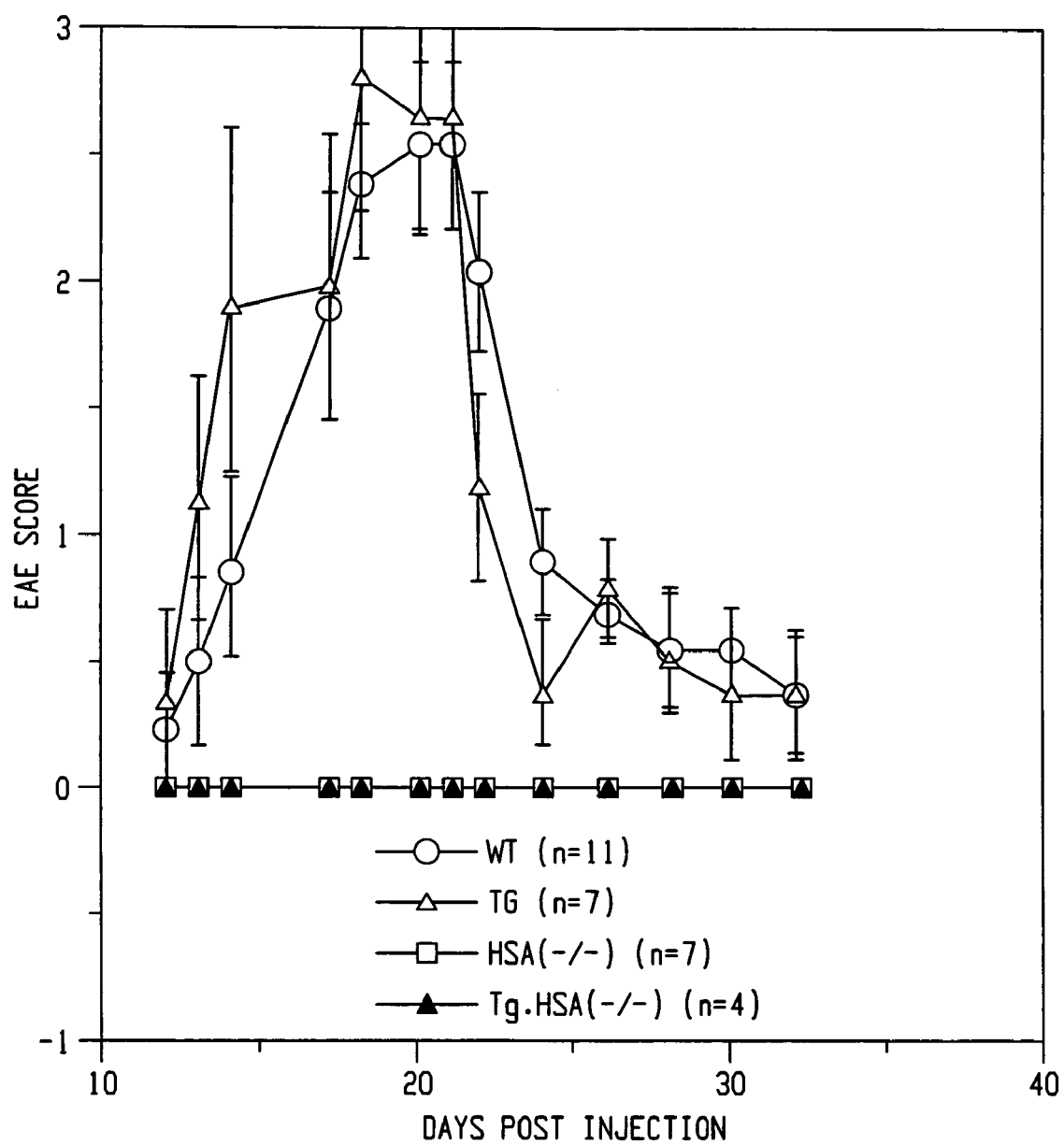

(22). For this study, We crossed the HSA transgene to HSA-deficient mice to produce mice that expressed HSA exclusively on T cells (FIG. 5a). To test if HSA expression on the T cell lineage is sufficient for EAE development, we immunized WT, HSA-TG, HSA(–/–) and HSATG HSA(–/–) mice with MOG. As shown in FIG. 5b, wild-type and HSATG mice developed EAE with essentially identical kinetics, which indicates that transgenic expression of HSA on T cells does not prevent the production and effector function of self-reactive T cells. Nevertheless, much like HSA (–/–) mice, the mice with exclusive HSA-expression on the T cell lineage failed to develop EAE. These results demonstrated clearly that HSA expression on T cell lineage alone is insufficient for EAE development.

Figure 6A:
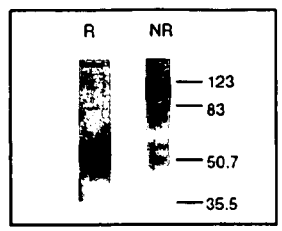
FIG. 6. HSAIg ameliorates EAE. a. Analysis of HSAIg by SDS-PAGE. 10 μg of purified HSAIg was separated by 10% reducing (R) and non-reducing SDS-PAGE. The proteins were stained by Comassie blue. The EAE score for control (PBS) or HSAIg-treated mice. EAE was induced in WT mice as described in Materials and Methods. On days 8, 10, 12, 14 and 22 after immunization, five mice per group were injected (i.p.) with 100 μg/mouse of either HSAIg or 100 ml of PBS as control. The effect of HSAIg has been evaluated in three independent experiments with similar results.
Figure 6B:
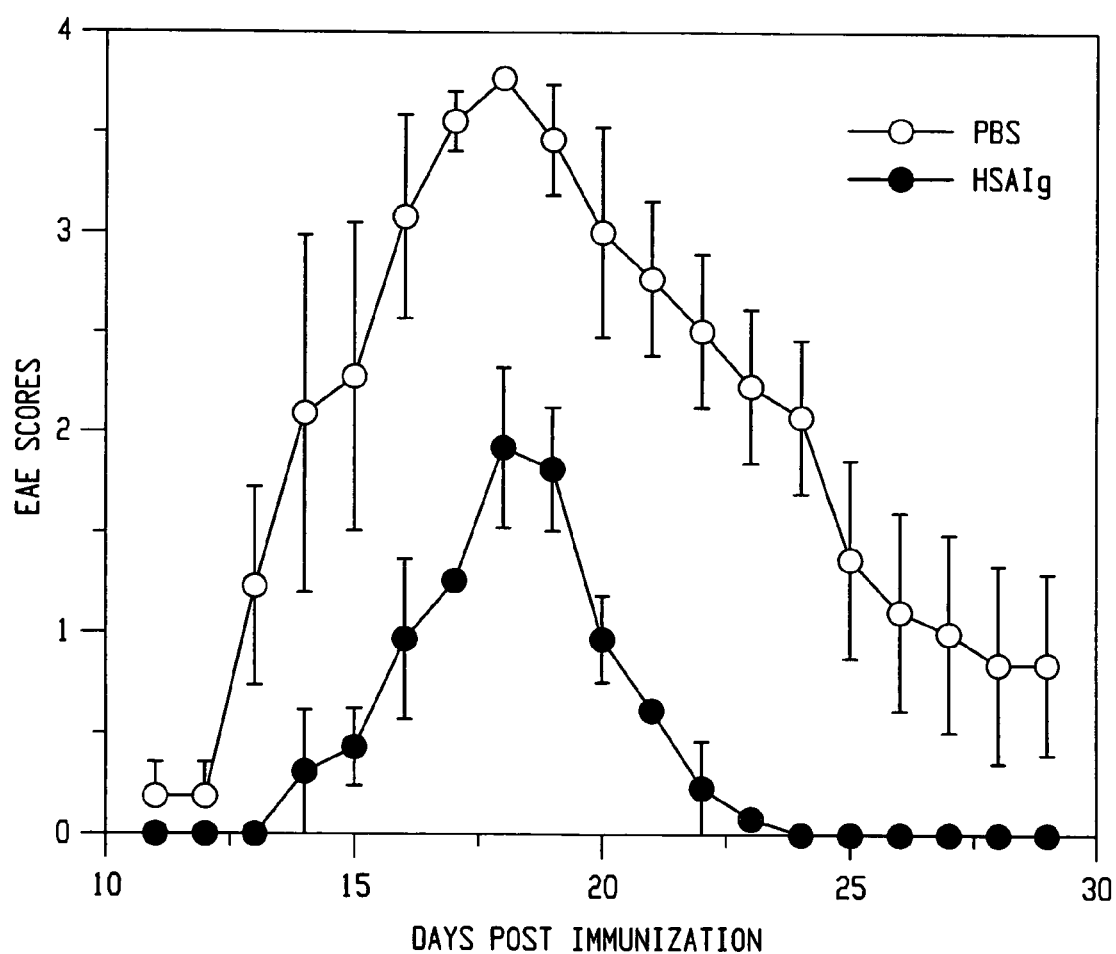
Figure 11A:
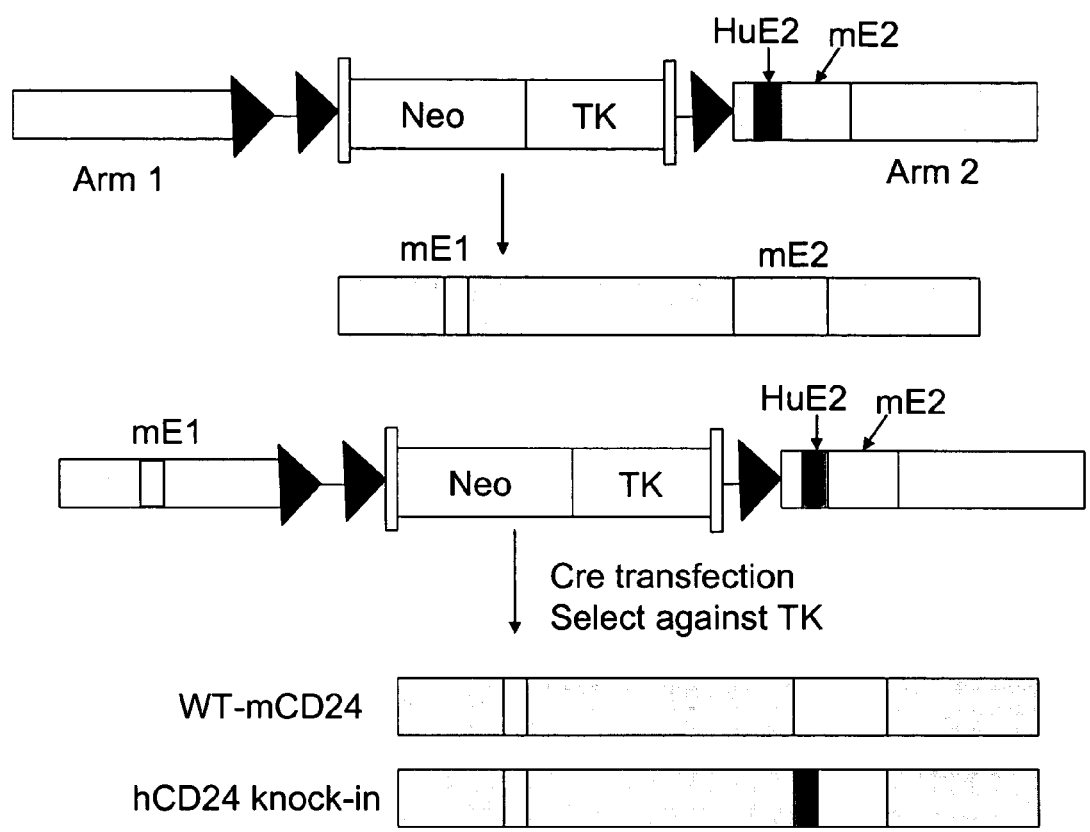
FIG. 11 is a diagram of a construct for producing human CD24 gene knock-in mice. Arm 1 of the knock in construct comprises nucleotide 2001 through nucleotide 5500 of the mouse HSA/CD14 gene, GenBank Accession No. X72910. Arm 2 of the construct is a chimera gene consisting of the last 262 by sequence of exon 1 of the mouse CD24 gene (SEQ ID NO: 30), the first 253 by sequence of exon 2 of the human CD24 gene (SEQ ID NO: 31) and about 3 kb of mouse CD24 sequence (SEQ ID NOS 32-33, respectively) which comprises remaining exon 2 sequence encoding for 3' untranslated region and 3' sequence of the mouse CD24 gene (SEQ ID NO: 22).
Figure 12:
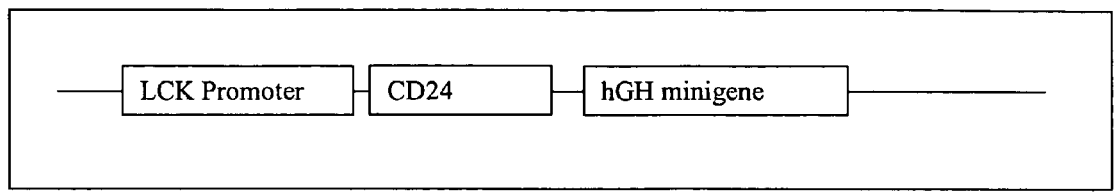
FIG. 12 is a diagram of a plasmid for producing transgenic mice expressing human CD24 in T cells. To produce this plasmid human CD24 coding sequence is subcloned into transgenic construct vector p1017 Barn HI site, which is described in EMBO J. 9: 3821-3829, 1990) CD24 forward primer (CD24F.Bam): G GCC GGA TCC ATG GGC AGA GCA ATG GTG (SEQ ID NO: 21) with BamHI site 5' to ATG start codon. CD24 reverse primer (CD24R. XhoBam): G GCC GGA TCC CTC GAG TTA AGA GTA GAG ATG CAG (SEQ ID NO: 23) with Barn HI and Xho I sites 3' to TAA stop codon.

The fact that HSA may be a critical checkpoint after activation of self-reactive T cells suggests a novel approach in treating autoimmune neurological diseases. Since an anti-HSA mAb was toxic in the EAE model to address this issue (Data not shown), we produced a fusion protein between the extracellular domain of HSA and the Fc portion of human IgG1, to block the HSA-mediated interactions. As shown in FIG. 6a, the fusion protein has an apparent molecular weight of about 100 kD under non-reducing SDS-PAGE. After reduction, it migrated as a 50 kD band. We treated mice starting at 8-10 days after immunization with MOG peptide, when MOG-specific T cells response had already expanded in the local lymph nodes. As shown in FIG. 6b, HSAIg drastically ameliorated EAE. All HSAIg-treated mice recovered substantially earlier than did the control mice. Since MOG-reactive T cells had been activated prior to HSAIg administration, the clinical signs in the treated group may reflect the fact that some autoreactive T cells had already migrated into the central nervous system.

HSAIg, a fusion protein consisting of the extracellular domain of mouse HAS and the Fc portion of immunoglobulin, drastically ameliorates the clinical sign of EAE even when administrated after self-reactive T cells had been expanded. Thus, identification of HSA as a novel checkpoint, even after activation and expansion of self-reactive T cells, provides a novel approach for immunotherapy of autoimmune neurological diseases, such as multiple sclerosis.

Example 2

Production Human CD24Ig Fusion Protein

Fragments of the human CD24 polypeptides lacking the GPI anchor region are fused with human Ig constant region to form CD24-Ig fusion protein. In one embodiment the CD24 polypeptide fragment comprises the signal peptide. In another embodiment the CD24 polypeptide fragment lacks the signal peptide. The fragment of the human CD24 coding sequence is subcloned into vector pIg (from Novagen) Hind III and BamHI sites. Suitable primers useful in subcloning include, but are not limited to, CD24 forward primer (CD24F.H3): G GCC MG CTT ATG GGC AGA GCA ATG GTG, SEQ ID NO.:9, with Hind III site 5' to ATG start codon. CD24-Ig reverse primer (CD24Rig.Bm): GG CCG GAT CCA CTT ACC TGT CGC CTT GGT GGT GGC ATT, SEQ ID NO.10, with Bam HI site and the SD sequence (A CTT ACC TGT, SEQ ID NO.:11) next to 3' end of TTKA (direct sequence: ACC ACC AAG GCG, SEQ ID NO.:12) in Human CD24. The construct is transfected into CHO cells, and the CD24Ig is secreted into the tissue culture medium. CD24Ig is purified by affinity chromatography using a Protein G column. The clone compresses CD24 signal peptide, CD24 core peptide and the IgG/Fc portion, but lacks the GPI anchor signaling region.

Example 3

Production of Anti-Human CD24 mAb that Blocks Autoreactive T Cells-Initiated Tissue Destruction Human CD24 coding sequence is subcloned into vector pCDM8 (from Invitrogen) Hind III and Xho I sites. CD24 forward primer (CD24F.H3): G GCC AAG CTT ATG GGC AGA GCA ATG GTG (SEQ ID NO: 9) with Hind III site 5' to ATG start codon. CD24 reverse primer (CD24R. Xho): A TCC CTC GAG TTA AGA GTA GAG ATG CAG (SEQ ID NO: 16) with Xho I site 3' to TAA stop codon. The CD24 cDNA is transfected into murine 3T3 cells. The 3T3 cell lines that stably express human CD24 molecules are used to immunize syngeneic mice. After 2-3 immunization, spleen cells are fused with myeloma AgX865, after selection with HAT medium the supernatants are screened for anti-human CD24 mAbs. The antibodies are tested for their ability to block both adhesion of human T cells to human endothelial cells in vitro, and their ability to block human CD24-mediated T cell trafficking to target tissues, such as the pancreas and the central nervous system using the transgenic model detailed below.

Example 4

Testing Putative Inhibitors of Multiple Sclerosis with CD24 Transgenic and Knock-in Mice The immunogen, MOG peptide 35-55 of rat origin (MEVGWYRSPFSRVVHLYRNGK, SEQ ID NO.:13), is available from Research Genetics, Inc. (Huntsville, Ala., USA). Mice of 8-12 wks of age are immunized subcutaneously with 200 µg MOG peptide in complete Freund's Adjuvant (400 µg of *Mycobacterium tuberculosis* per ml) in a total volume of 100 µl. They receive 200 µg of Pertusis toxin (List Biological, Campbell, Calif.) in 200 Id PBS in the tail vein immediately after the immunization, and again 48 hours later. The mice are observed every other day and scored on a scale of 0-5 with gradations of 0.5 for intermediate scores: 0, no clinical signs; 1, loss of tail tone; 2, wobbly gait; 3, hind limb paralysis; 4, hind and fore limb paralysis; 5, death. The putative inhibitory molecules are injected at 1 week after immunization. Those that substantially reduce the clinical score of EAE are selected for further testing.

Example 5

Generation of Human CD24 Gene Knock-in Mice

The basic strategy used to produce CD24 gene knock-in mice is to replace part of murine CD24 gene exon 2 sequence with that of human CD24 sequence. We took advantage of the fact that signal peptide, encoded by exon 1 of mouse and human CD24 gene, are identical between mouse and human CD24. We therefore replaced only part of the mouse exon 2 sequence with that of 240 bp of human CD24. The construct with the desired sequence is shown in FIG. 13.

Figure 13:
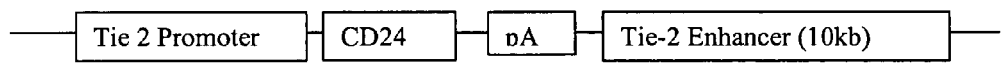
FIG. 13 is a diagram of a vector for producing mice that express CD24 in vascular endothelial cells.

As shown in FIG. 13, arm 1 of the construct comprised of a 2.7 kb fragment of mouse CD24 gene, cloned from 129RI ES cells (Seq ID. 20). The arm 2 of the construct is a chimera gene consisting of the last 256 bp sequence of CD24 exon 1, first 240 bp human CD24 exon 2 sequence and about 3 kb of mouse CD25 sequence comprising of both remaining exon 2 sequence encoding for 3' untranslated region and 3' sequence of the CD24 gene Seq I.D. 22). The construct is used to transfect ES cells. The recombinants are screened by procedures established in the art, including PCR and Southern blot. The ES cells with the illustrated knock-in alleles are transfected with plasmid encoding Cre recombinase that recognize the lox P sequence. Since ES cells expression CD24 gene, as revealed by cell surface flow cytometry, the functionality of the knock-in alleles can be confirmed by cell surface expression of human CD24. The ES cells with the capacity to express human CD24 are used to produce chimera mice by blastocyte injection according to technique known in the art. Mice with germ-line transmission are produced by breeding the chimera mice.

Example 6

Inhibition of CD24 Expression by dsRNAi Technology

Mouse and human CD24 genes are highly homologous. It is therefore possible to select regions that are identical between mouse and human CD24 as target for dsRNAi drug. An alignment between Human CD24 (XM_099027) and Mouse CD24 (NM_009846) is shown in FIG. 14. Eight regions with a stretch of identical nucleotide that is 17 bp or longer are highlighted and as preferred target sequences. Although identity between mouse and human is not an essential feature of the dsRNAi molecule, targeting the dsRNAi to identical regions provides a dsRNAi which can be used to inhibit expression of both mouse and human CD24 genes. As a result, preclinical small rodent models can be used to screen for the efficacy of dsRNAi molecule in animal disease models, in addition to cell culture.

CHO cells transfected with either mouse or human CD24 cDNA are transfected with dsRNAi, produced by in vitro annealing. Briefly, both sense and antisense RNA corresponding to nt. 46-64 (+1 as translation starting site) of mouse and human CD24 gene plus two thymidine were synthesized by a commercial vendors. The sequence of the two strands are as follows: CD24-46/64 iRNA.F: 5'-CUG GCA CUG CUC CUA CCC ATT-3' (SEQ ID NO: 20), and CD24-46/64 iRNA.R: 5'-UGG GUA GGA GCA GUG CCA GTT-3' (SEQ ID NO: 17). Control oligonucleotides were designed based the inverted sequence, as follows invCD24-46/64 iRNA.F: 5'-ACC CAU CCU CGU CAC GGU C TT ' (SEQ ID NO: 18) invCD24-46/64 iRNA.R: 5'-GAC CGU GAC GAG GAU GGG UTT-3' (SEQ ID NO: 19). For annealing of siRNA, 20 uM single strands will be incubated in annealing buffer 100 mM KOAc, 30 mM HEPES at pH7.4, 2 mM MgAc) for 1 min at 94 degree followed by 1h at 37 degree and resulting dsRNA. The resulting dsRNAi is used to transfect CHO cells. At 48 hours after transfection, the cells are analyzed for CD24 expression by flow cytometry.

Figure 15:
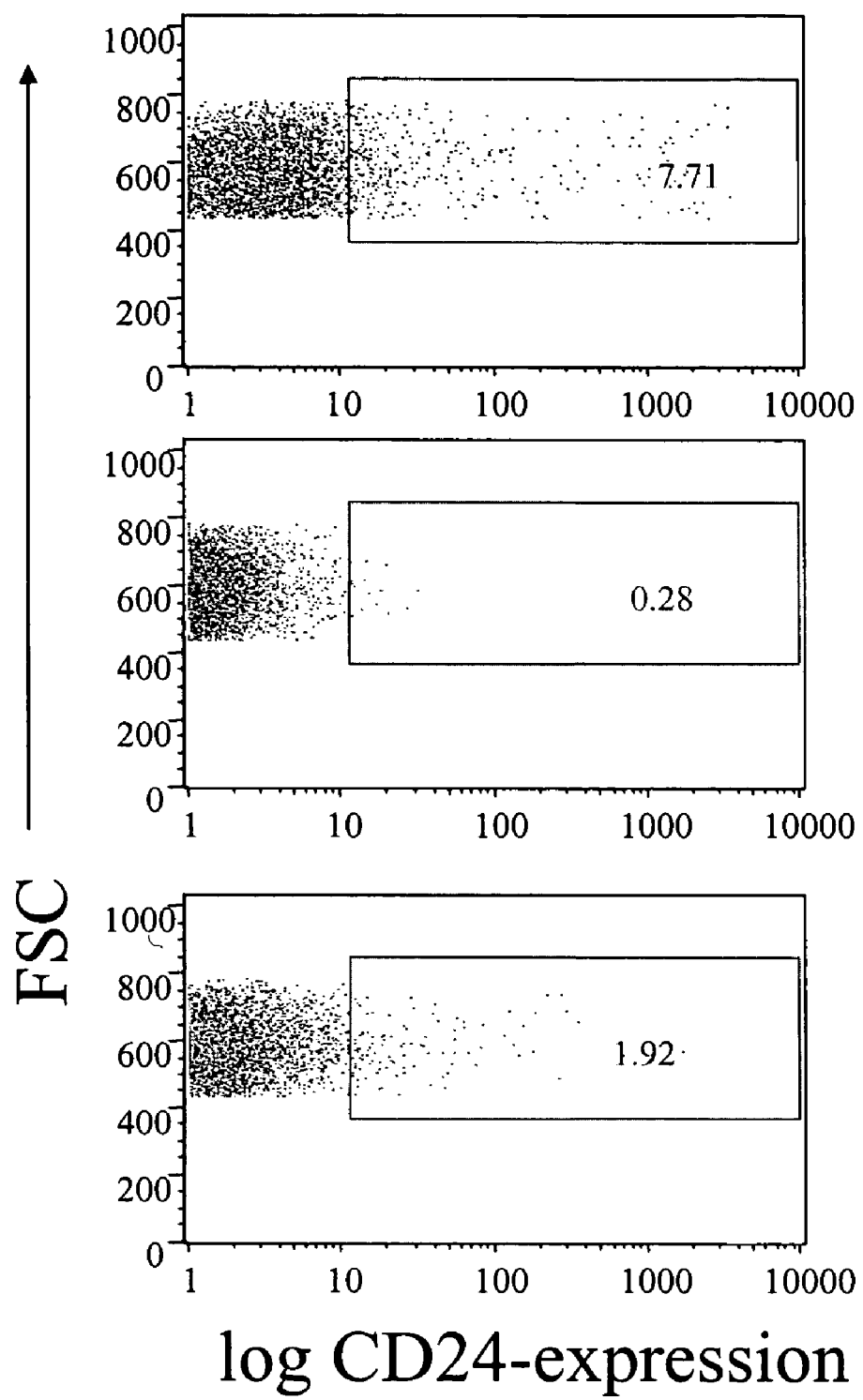

As shown in FIG. 15, transient transfection lead to expression of CD24 on about 7% of the CHO cells. Inverted dsRNA reduced expression of CD24 some what, although significant number of CHO cells (2%) still express high level of CD24. Importantly, the expression of CD24 is completely abrogated when the CHO cells are co-transfected with dsRNAi corresponding to human/mouse CD24 sequence. These results revealed that the dsRNAi can be used to inhibit expression of CD24.

What is claimed is:

1. A method for treating a human patient suspected of having, known to have, or predisposed to having multiple sclerosis, said method comprising:

administering to said patient a pharmaceutical composition comprising an isolated human HSA/CD24 polypeptide fusion and a physiologically acceptable carrier, wherein the HSA/CD24 polypeptide fusion comprises a HSA/CD24 core region, wherein the HSA/CD24 fusion comprises the HSA/CD24 polypeptide linked by a peptide bond to the hinge-CH2-CH3 region of human immunoglobulin G1, and wherein the HSA/CD24 polypeptide fusion is glycosylated.

2. The method of claim 1, wherein the HSA/CD24 polypeptide fusion is produced by expression in a mammalian host cell.

3. The method of claim 1, wherein the pharmaceutical composition is administered when the patient has clinical symptoms of multiple sclerosis.

4. The method of claim 1, wherein the pharmaceutical composition is administered when the patient is in temporary remission from symptoms of multiple sclerosis.

5. The method of claim 1, wherein the HSA/CD24 polypeptide fusion further comprises the N-terminal HSA/CD24 signal peptide.

6. The method of claim 2, wherein the host cell is a CHO cell.

* * * * *

UNITED STATES PATENT AND TRADEMARK OFFICE
CERTIFICATE OF CORRECTION

PATENT NO. : 7,744,894 B2
APPLICATION NO. : 11/129083
DATED : June 29, 2010
INVENTOR(S) : Yang Liu, Pan Zheng and Xuefeng Bai It is certified that error appears in the above-identified patent and that said Letters Patent is hereby corrected as shown below:

In the Specification

Column 1, Lines 19-21 replace the Government Support Clause with:
--This invention was made with government support under grant number AI032981 awarded by National Institutes of Health. The government has certain rights in the invention.--

Signed and Sealed this
Sixth Day of October, 2020

Andrei Iancu
*Director of the United States Patent and Trademark Office*

SEQUENCE LISTING

<160> NUMBER OF SEQ ID NOS: 33

<210> SEQ ID NO 1
<211> LENGTH: 76
<212> TYPE: PRT
<213> ORGANISM: Mus musculus

<400> SEQUENCE: 1

Met Gly Arg Ala Met Val Ala Arg Leu Gly Leu Gly Leu Leu Leu Leu
 1               5                  10                  15

Ala Leu Leu Leu Pro Thr Gln Ile Tyr Cys Asn Gln Thr Ser Val Ala
            20                  25                  30

Pro Phe Pro Gly Asn Gln Asn Ile Ser Ala Ser Pro Asn Pro Ser Asn
        35                  40                  45

Ala Thr Thr Arg Gly Gly Gly Ser Ser Leu Gln Ser Thr Ala Gly Leu
    50                  55                  60

Leu Ala Leu Ser Leu Ser Leu Leu His Leu Tyr Cys
65                  70                  75

<210> SEQ ID NO 2
<211> LENGTH: 80
<212> TYPE: PRT
<213> ORGANISM: Homo sapiens

<400> SEQUENCE: 2

Met Gly Arg Ala Met Val Ala Arg Leu Gly Leu Gly Leu Leu Leu Leu
 1               5                  10                  15

```
Ala Leu Leu Leu Pro Thr Gln Ile Tyr Ser Ser Glu Thr Thr Thr Gly
             20                  25                  30

Thr Ser Ser Asn Ser Ser Gln Ser Thr Ser Asn Ser Gly Leu Ala Pro
         35                  40                  45

Asn Pro Thr Asn Ala Thr Thr Lys Val Ala Gly Gly Ala Leu Gln Ser
 50                  55                  60

Thr Ala Ser Leu Phe Val Val Ser Leu Ser Leu Leu His Leu Tyr Ser
 65                  70                  75                  80

<210> SEQ ID NO 3
<211> LENGTH: 76
<212> TYPE: PRT
<213> ORGANISM: Rattus norvegicus

<400> SEQUENCE: 3

Met Gly Arg Ala Met Val Val Arg Leu Gly Leu Gly Leu Leu Leu Leu
 1               5                  10                  15

Ala Leu Leu Leu Pro Thr Gln Ile Tyr Cys Asn Gln Thr Ser Val Ala
             20                  25                  30

Pro Phe Ser Gly Asn Gln Ser Ile Ser Ala Ala Pro Asn Pro Thr Asn
         35                  40                  45

Ala Thr Thr Arg Ser Gly Cys Ser Ser Leu Gln Ser Thr Ala Gly Leu
 50                  55                  60

Leu Ala Leu Ser Leu Ser Leu Leu His Leu Tyr Cys
 65                  70                  75

<210> SEQ ID NO 4
<211> LENGTH: 1494
<212> TYPE: DNA
<213> ORGANISM: Artificial Sequence
<220> FEATURE:
<223> OTHER INFORMATION: Description of Artificial Sequence: Synthetic
      fusion gene

<400> SEQUENCE: 4
atgggcagag cgatgggggc caggctaggg ctggggttgc tgcttctggc actgctccta      60
cccacgcaga tttactgcaa ccaaacatct gttgcaccgt ttcccggtaa ccagaatatt     120
tctgcttccc caaatccaag taacgctacc accagagatc ccgagggtga gtactaagct     180
agcttcagcg ctcctgcctg gacgcatccc ggctatgcag ccccagtcca gggcagcaag     240 gcaggcccg tctgcctctt cacccggagc ctctgcccgc ccactcatg ctcaggaga       300 gggtcttctg gctttttccc aggctctggg caggcacagg ctaggtgccc ctaacccagg     360
ccctgcacac aaaggggcag gtgctgggct cagacctgcc aagagccata tccgggagga     420 ccctgccccct gacctaagcc caccccaaag gccaaactct ccactccctc agccggacac     480
cttctctcct cccagattcc agtaactccc aatcttctct ctgcagagcc caaatcttgt     540
gacaaaactc acacatgccc accgtgccca ggtaagccag cccaggcctc gcctccagc      600 tcaaggcggg acaggtgccc tagagtagcc tgcatccagg acaggcccc agccgggtgc      660 tgacacgtcc acctccatct cttcctcagc acctgaactc ctgggggac cgtcagtctt      720 cctcttcccc ccaaaaccca aggacaccct catgatctcc cggacccctg aggtcacatg     780
cgtggtggtg gacgtgagcc acgaagaccc tgaggtcaag ttcaactggt acgtggacgg     840
cgtggaggtg cataatgcca agacaaagcc gcgggaggag cagtacaaca gcacgtaccg     900
ggtggtcagc gtcctcaccg tcctgcacca ggactggctg aatggcaagg agtacaagtg     960
caaggtctcc aacaaagccc tcccagcccc catcgagaaa accatctcca aagccaaagg    1020
```

-continued

```
tgggacccgt ggggtgcgag ggccacatgg acagaggccg gctcggccca ccctctgccc    1080
tgagagtgac cgctgtacca acctctgtcc tacagggcag ccccgagaac cacaggtgta    1140
caccctgccc ccatcccggg atgagctgac caagaaccag gtcagcctga cctgcctggt    1200
caaaggcttc tatcccagcg acatcgccgt ggagtgggag agcaatgggc agccggagaa    1260
caactacaag accacgcctc ccgtgctgga ctccgacggc tccttcttcc tctacagcaa    1320
gctcaccgtg gacaagagca ggtggcagca ggggaacgtc ttctcatgct ccgtgatgca    1380
tgaggctctg cacaaccact acacgcagaa gagcctctcc ctgtctccgg gtaaatgagt    1440
gcgacggccg gcaagccccg ctccccgggc tctcgcggtc gcacgaggat gctt          1494
```

<210> SEQ ID NO 5
<211> LENGTH: 864
<212> TYPE: DNA
<213> ORGANISM: Artificial Sequence
<220> FEATURE:
<223> OTHER INFORMATION: Description of Artificial Sequence: Synthetic fusion gene

<400> SEQUENCE: 5

```
atgggcagag cgatgggggc caggctaggg ctggggttgc tgcttctggc actgctccta     60
cccacgcaga tttactgcaa ccaaacatct gttgcaccgt ttcccggtaa ccagaatatt    120
tctgcttccc caaatccaag taacgctacc accagagatc ccgaggagcc caaatcttgt    180
gacaaaactc acacatgccc accgtgccca ggcacctgaa ctcctggggg gaccgtcagt    240
cttcctcttc cccccaaaac ccaaggacac cctcatgatc tcccggaccc ctgaggtcac    300
atgcgtggtg gtggacgtga gccacgaaga ccctgaggtc aagttcaact ggtacgtgga    360
cggcgtggag gtgcataatg ccaagacaaa gccgcgggag gagcagtaca acagcacgta    420
ccgggtggtc agcgtcctca ccgtcctgca ccaggactgg ctgaatggca aggagtacaa    480
gtgcaaggtc tccaacaaag ccctcccagc ccccatcgag aaaaccatct ccaaagccaa    540
aggcagcccc gagaaccaca ggtgtacacc ctgcccccat cccgggatga gctgaccaag    600
aaccaggtca gcctgacctg cctggtcaaa ggcttctatc ccagcgacat cgccgtggag    660
tgggagagca atgggcagcc ggagaacaac tacaagacca cgcctcccgt gctggactcc    720
gacggctcct tcttcctcta cagcaagctc accgtggaca agagcaggtg gcagcagggg    780
aacgtcttct catgctccgt gatgcatgag gctctgcaca accactacac gcagaagagc    840
ctctccctgt ctccgggtaa atga                                          864
```

<210> SEQ ID NO 6
<211> LENGTH: 20
<212> TYPE: DNA
<213> ORGANISM: Mus musculus

<400> SEQUENCE: 6

```
ggaaagctta tgggcagagc                                                20
```

<210> SEQ ID NO 7
<211> LENGTH: 20
<212> TYPE: DNA
<213> ORGANISM: Mus musculus

<400> SEQUENCE: 7

```
cgagatctct ggtggtagcg                                                20
```

<210> SEQ ID NO 8
<211> LENGTH: 41
<212> TYPE: DNA
<213> ORGANISM: Homo sapiens

<400> SEQUENCE: 8
cttcgaccag tctagaagca tcctcgtgcg accgcgagag c                          41

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggccaagctt atgggcagag caatggtg                                        28

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggccggatcc acttacctgt cgccttggtg gtggcatt                             38

<210> SEQ ID NO 11
<211> LENGTH: 10
<212> TYPE: DNA
<213> ORGANISM: Homo sapiens

<400> SEQUENCE: 11
acttacctgt                                                            10

<210> SEQ ID NO 12
<211> LENGTH: 12
<212> TYPE: DNA
<213> ORGANISM: Homalozoon vermiculare

<400> SEQUENCE: 12
accaccaagg cg                                                         12

<210> SEQ ID NO 13
<211> LENGTH: 21
<212> TYPE: PRT
<213> ORGANISM: Rattus norvegicus

<400> SEQUENCE: 13

Met Glu Val Gly Trp Tyr Arg Ser Pro Phe Ser Arg Val Val His Leu
 1               5                  10                  15

Tyr Arg Asn Gly Lys
            20

<210> SEQ ID NO 14
<211> LENGTH: 287
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 14

```
Met Gly Arg Ala Met Gly Ala Arg Leu Gly Leu Gly Leu Leu Leu Leu
  1               5                  10                  15

Ala Leu Leu Leu Pro Thr Gln Ile Tyr Cys Asn Gln Thr Ser Val Ala
             20                  25                  30

Pro Phe Pro Gly Asn Gln Asn Ile Ser Ala Ser Pro Asn Pro Ser Asn
         35                  40                  45

Ala Thr Thr Arg Asp Pro Glu Glu Pro Lys Ser Cys Asp Lys Thr His
     50                  55                  60

Thr Cys Pro Pro Cys Pro Ala Pro Glu Leu Leu Gly Gly Pro Ser Val
 65                  70                  75                  80

Phe Leu Phe Pro Pro Lys Pro Lys Asp Thr Leu Met Ile Ser Arg Thr
                 85                  90                  95

Pro Glu Val Thr Cys Val Val Val Asp Val Ser His Glu Asp Pro Glu
             100                 105                 110

Val Lys Phe Asn Trp Tyr Val Asp Gly Val Glu Val His Asn Ala Lys
         115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                 165                 170                 175

Ser Lys Ala Lys Gly Gln Pro Arg Glu Pro Gln Val Tyr Thr Leu Pro
             180                 185                 190

Pro Ser Arg Asp Glu Leu Thr Lys Asn Gln Val Ser Leu Thr Cys Leu
         195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                 245                 250                 255

Trp Gln Gln Gly Asn Val Phe Ser Cys Ser Val Met His Glu Ala Leu
             260                 265                 270

His Asn His Tyr Thr Gln Lys Ser Leu Ser Leu Ser Pro Gly Lys
         275                 280                 285

<210> SEQ ID NO 15
<211> LENGTH: 48
<212> TYPE: DNA
<213> ORGANISM: Homo sapiens

<400> SEQUENCE: 15
cagggatccc gagggtgagt actaagctag cttcagcgct cctgcctg         48

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atccctcgag ttaagagtag agatgcag                               28
```

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
uggguaggag cagugccagt t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
acccauccuc gucacgguct t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
gaccgugacg aggaugggut t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
cuggcacugc uccuacccat t                                              21

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggccggatcc atgggcagag caatggtg                                       28

<210> SEQ ID NO 22
<211> LENGTH: 3475

<212> TYPE: DNA
<213> ORGANISM: Artificial Sequence
<220> FEATURE:
<223> OTHER INFORMATION: Description of Artificial Sequence: Synthetic Chimeric Gene Construct

<400> SEQUENCE: 22

```
ttcaggaatt cagaatttga aatgcggcta agagaacaat gtggggaaaa aagagtctta      60
gggcggatca gggactggag agtgtaattc agtggtggag cgtgaatact tagtgtccct     120
aagaccctgt gtttggcttc tacctgcagc tacagagact attatctgct tgagtgttat     180
tacagagtgc aaatggagat agctgtggat ggttctgaaa tttatctgtg atttcttttt     240
ccttatttat tttagattta ctagatttac tcgagtgaaa caacaactgg aacttcaagt     300
aactcctccc agagtacttc caacactggg ttggccccaa atccaactaa tgccaccacc     360
aaggcggctg gtggtgccct gcagtcaaca gccagtctct tcgtggtctc actctctctt     420
ctgcatctct actcttaaga gactcaggcc aagaaacgtc ttctaaactt ccccatcttc     480
taaacccaat ccaaatggcg tctggaagtc caatgaagtc caatgtgatc aggaagaaac     540
aggtccacct cgaattggct gttaccatat ctcaacagaa aacacggaga attcgaaatt     600
cgacgggatt aaaggacgcg tgaaaggttt gagagaagag agatgccgct attgaatctg     660
ctggagtttt acatcccaag atgaagacag cattcagaat tgatgtgatt ccttgaatg      720
tggcttagga aatgtggaca cttaaaactc tcacttgaaa ttgggcacag gtttgatgta     780
gagataagga cggggtgcgg aatggagacc cattttgtca ttgattcatc tgaccgataa     840
ggccatagtg cagttaggtg atattcgaag cttctttgat gctctttatg tatatgttgg     900
aaggaactac caggcgttgc tttaaattcc aatgtgttg tttcgttact actaatttaa      960
taccgtaagc tctaggtaaa gttccatgtt gttgaactct gactgttctc tttggaattg    1020
aacgttttgc atcctcctcc tgtggcttta ggtctgacat tgtatttgac ctttactagt    1080
aattaacatg tgccaggcaa tggtggattg gaacccatcc ccaagtccag ccaccactga    1140
ataaatctga tttcaaaagt caaacagtag acatttccca ttgtcgtttc tcactcacca    1200
caagcaccaa attcactaga gtacactggt tccagagagc agaatcatgt tggccttggc    1260
taatttcaaa atgctgtctt ttactttggt atatgttgag ggcttttcat aatttaaagt    1320
gtgttctgtt agcaaggcaa aaattatgag tcttaattct acaggcaaat atgcaaagga    1380
gccaaaactg taaacccagc atttgggatg tgaagactgg aagctaactc tcattgaatt    1440
cacaaagtct tttatacgat ttctgtacat acttttttt tttttaagag aaaaacaaac     1500
ggtggatcag aatagccacg tttgaatac tttggttatc cattcatatt tttagatagt    1560
tattggtcct gtgcctgaaa gggggcttgg ttctaccgta agttttttcca atttccttga    1620
tatacacata ccttctaaaa cctagacatt tcctgaaaaa aatcttttgt tcgcatggtc    1680
acacactgat gcttacccgt acagtagtct tgataaccag agtcattttc tccatcttta    1740
gaaaccttcc tgggaagaag gagagctcac agacccgaag ctactgtgtg tgtgaatgaa    1800
cactccctt gcctcacacc tgaatgctgt acatctattt gattgtaaat tgtgtttgtg     1860
tatttatgct ttgattcata gtaacttctc atgttatgga attgatttgc attgaacaca    1920
aactgtaaat aaaagaaaga aatggcggag agagcagtct gttgaattta tttacttact    1980
ttttaaaaag acttatttat tttatgtatg tgagtatatc gaagttgttt tcagacacac    2040
cagaagaggg tatcagatgg ttgtgagcca ctgtgtggtt gctgggaatt gaactcagga    2100
cctctagaag ggtagccagt gctcttaacc actgagccat ctctccagcc cccagtctgt    2160
```

```
tgaatttaaa gtgtttcttg agcaataatt atgggtgatc atggctgtta agggatatat    2220
cttgttctac taactagaac attacatgct gtctattttt gaaaggccag ctagcagcag    2280
gtttggtttc ctcccaaagc tgctccccccc cttccaagtg ctgggaataa aggcgtgtgc   2340
ctccacgcct gtctctagtt gacatcttta agcttttaag gttgtacacc tacttgctca    2400
gcaactgaga gccagctgtg tgccaaggta cccatgactg atgaagttgg ctggggagag    2460
agtctttgag atgagaggtc tctggtttgc caggcagggc tcttaggaca acaccagcag    2520
ggcagggctc tgggaccaca gattgagaac ccacaatggc cttgaacctt agacctgaat    2580
gacaggtgtt ggtgggagaa catgagcgga aattttcgtg gaatgaacag cttctaagtc    2640
acctctactt tctcttaccg gcccagaggt ctacacctca ctttggtttt ctaaattggc    2700
tctcccctgc ttttttccata tatcaaacac attcctggat tcctaacatc tttactgtga   2760
ttcagggacc accagaaagg gcaggctgga aactgctgtt cttaggcaga gttccataag    2820
aaacctcagg tctaccctttt aagacttaga tgatctggag ctctcttcaa tgatgtctac    2880
agattgccct ccccgctgca ccccactccg cagccatatg aagtatacta ggttggtgtg    2940
ggggtaactg agaactactt attgacatgt aaactggtca ccacagttca ttgtctcagc    3000
atgttttgtc tccagatgaa caatagcctc tctctagtag agaagtgtct tgcacacaaa    3060
cagaaacatt tcccagaagt gccagtgtcg ttcattcatc ctactttggt ttaagtgtct    3120
gattgttttt tgttttggaa actgtctcat tctgtatgta gcctaggctg gtctcaaact    3180
tagggtggtc ttacctcagt ctcctgagcc ccgggcttgt gtcgtcacac ccagcttttc    3240
tgtgttttgt ttttggttt tgttttgttt tgaaacaggg ttttgctatg tgacttaggc      3300
atactatgta gcctgggctg gccttgaact catggacatc tgcctctgtt tcctgagagc    3360
tagagttaca gatgtgtgtc acttatgttc actcttagta tcctgtgatt tatgttagat    3420
attactgaaa attattacta aatcttgtca gttgtagata cgatgggaga atgta          3475

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggccggatcc ctcgagttaa gagtagagat gcag                                34

<210> SEQ ID NO 24
<211> LENGTH: 154
<212> TYPE: DNA
<213> ORGANISM: Homo sapiens

<400> SEQUENCE: 24
gaagctactg tgtgtgtgaa tgaacactct tttgctttat tccagaatgc tgtacatcta    60
ttttggattg tatattgtgt ttgtgtattt acgctttgat tcatagtaac ttcttatgga    120
attgatttgc attgaacaca aactgtaaat aaaa                                154

<210> SEQ ID NO 25
<211> LENGTH: 158
<212> TYPE: DNA
<213> ORGANISM: Mus musculus

<400> SEQUENCE: 25
```

```
gaagctactg tgtgtgtgaa tgaacactcc ccttgcctca cacctgaatg ctgtacatct    60
atttgattgt aaattgtgtt tgtgtattta tgctttgatt catagtaact tctcatgtta   120
tggaattgat ttgcattgaa cacaaactgt aaataaaa                           158

<210> SEQ ID NO 26
<211> LENGTH: 327
<212> TYPE: DNA
<213> ORGANISM: Homo sapiens
<220> FEATURE:
<221> NAME/KEY: modified_base
<222> LOCATION: (109)..(116)
<223> OTHER INFORMATION: Variable base

<400> SEQUENCE: 26
aggcaaaaat gtaaaggagt caaaactaca aatcaagtat ttgggaagtg aagactggaa    60
gctaatttgc attaaattca caaacttttta tactcttctt gtatatacnn nnnnnncttt  120
aaaaaacaac tatggatcag aatagccaca tttggaatac ttttttgttat cagtcaatat  180 ttttagatag ttagaacctg gtcctaagcc taaaagtggg cttgattctg cagtaaatct  240
tttacaactg cctcgaaaca cagaaacctt tttaaaaata gacactcccc gaagtctttt  300
gttcgcatgg tcacacactg atgctta                                       327

<210> SEQ ID NO 27
<211> LENGTH: 273
<212> TYPE: DNA
<213> ORGANISM: Mus musculus

<400> SEQUENCE: 27
aggcaaatat gcaaaggagc caaaactgta aacccagcat ttgggatgtg aagactggaa    60
tttaagagaa aaacaaacgg tggatcagaa tagccacgtt tggaatactt tggttatcca  120
ttcatatttt tagatagtta ttggtcctgt gcctgaaagg gggcttggtt ctaccgtaag  180 ttttttccaat ttccttgata tacacatacc ttctaaaacc tagacatttc ctgaaaaaaa 240
tcttttgttc gcatggtcac acactgatgc tta                                273

<210> SEQ ID NO 28
<211> LENGTH: 39
<212> TYPE: DNA
<213> ORGANISM: Homo sapiens

<400> SEQUENCE: 28
gctgctgctg ctggcactgc tcctacccac gcagattta                           39

<210> SEQ ID NO 29
<211> LENGTH: 39
<212> TYPE: DNA
<213> ORGANISM: Mus musculus

<400> SEQUENCE: 29
gttgctgctt ctggcactgc tcctacccac gcagattta                           39

<210> SEQ ID NO 30
<211> LENGTH: 262
<212> TYPE: DNA
<213> ORGANISM: Mus musculus

<400> SEQUENCE: 30
ttcaggaatt cagaatttga aatgcggcta agagaacaat gtggggaaaa aagagtctta    60
```

| | |
|---|---|
| gggcggatca gggactggag agtgtaattc agtggtggag cgtgaatact tagtgtccct | 120 |
| aagaccctgt gtttggcttc tacctgcagc tacagagact attatctgct tgagtgttat | 180 |
| tacagagtgc aaatggagat agctgtggat ggttctgaaa tttatctgtg atttcttttt | 240 |
| ccttatttat tttagattta ct | 262 |

<210> SEQ ID NO 31
<211> LENGTH: 253
<212> TYPE: DNA
<213> ORGANISM: Homo sapiens

<400> SEQUENCE: 31

| | |
|---|---|
| agatttactc gagtgaaaca acaactggaa cttcaagtaa ctcctcccag agtacttcca | 60 |
| acactgggtt ggccccaaat ccaactaatg ccaccaccaa ggcggctggt ggtgccctgc | 120 |
| agtcaacagc cagtctcttc gtggtctcac tctctcttct gcatctctac tcttaagaga | 180 |
| ctcaggccaa gaaacgtctt ctaaacttcc ccatcttcta aacccaatcc aaatggcgtc | 240 |
| tggaagtcca atg | 253 |

<210> SEQ ID NO 32
<211> LENGTH: 1587
<212> TYPE: DNA
<213> ORGANISM: Mus musculus

<400> SEQUENCE: 32

| | |
|---|---|
| aagtccaatg tgatcaggaa gaaacaggtc cacctcgaat tggctgttac catatctcaa | 60 |
| cagaaaacac ggagaattcg aaattcgacg ggattaaagg acgcgtgaaa ggtttgagag | 120 |
| aagagagatg ccgctattga atctgctgga gttttacatc ccaagatgaa gacagcattc | 180 |
| agaattgatg tgatttcctt gaatgtggct taggaaatgt ggacacttaa aactctcact | 240 |
| tgaaattggg cacaggtttg atgtagagat aaggacgggg tgcggaatgg agacccattt | 300 |
| tgtcattgat tcatctgacc gataaggcca tagtgcagtt aggtgatatt cgaagcttct | 360 |
| ttgatgctct ttatgtatat gttggaagga actaccaggc gttgctttaa attcccaatg | 420 |
| tgttgtttcg ttactactaa tttaataccg taagctctag gtaaagttcc atgttgttga | 480 |
| actctgactg ttctctcttgg aattgaacgt tttgcatcct cctcctgtgg ctttaggtct | 540 |
| gacattgtat ttgaccttta ctagtaatta acatgtgcca ggcaatggtg gattggaacc | 600 |
| catccccaag tccagccacc actgaataaa tctgatttca aaagtcaaac agtagacatt | 660 |
| tcccattgtc gtttctcact caccacaagc accaaattca ctagagtaca ctggttccag | 720 |
| agagcagaat catgttggcc ttggctaatt tcaaaatgct gtcttttact ttggtatatg | 780 |
| ttgagggctt ttcataattt aaagtgtgtt ctgttagcaa ggcaaaaatt atgagtctta | 840 |
| attctacagg caaatatgca aaggagccaa aactgtaaac ccagcatttg ggatgtgaag | 900 |
| actgaagct aactctcatt gaattcacaa agtctttat acgatttctg tacatacttt | 960 |
| tttttttttt aagagaaaaa caaacggtgg atcagaatag ccacgtttgg aatactttgg | 1020 |
| ttatccattc atatttttag atagttattg gtcctgtgcc tgaaagggg cttggttcta | 1080 |
| ccgtaagttt ttccaatttc cttgatatac atacccttc taaaacctag acatttcctg | 1140 |
| aaaaaaatct tttgttcgca tggtcacaca ctgatgctta cccgtacagt agtcttgata | 1200 |
| accagagtca ttttctccat ctttagaaac cttcctggga agaaggagag ctcacagacc | 1260 |
| cgaagctact gtgtgtgtga atgaacactc cccttgcctc acacctgaat gctgtacatc | 1320 |
| tatttgattg taaattgtgt tgtgtatttt atgctttgat tcatagtaac ttctcatgtt | 1380 |

```
atggaattga tttgcattga acacaaactg taaataaaag aaagaaatgg cggagagagc    1440
agtctgttga atttatttac ttactttta aaaagactta tttattttat gtatgtgagt    1500
atatcgaagt tgttttcaga cacaccagaa gagggtatca gatggttgtg agccactgtg    1560
tggttgctgg gaattgaact caggacc                                       1587
```

<210> SEQ ID NO 33
<211> LENGTH: 1373
<212> TYPE: DNA
<213> ORGANISM: Mus musculus

<400> SEQUENCE: 33

```
tctagaaggg tagccagtgc tcttaaccac tgagccatct ctccagcccc cagtctgttg      60
aatttaaagt gtttcttgag caataattat gggtgatcat ggctgttaag ggatatatct     120
tgttctacta actagaacat tacatgctgt ctatttttga aaggccagct agcagcaggt     180
ttggtttcct cccaaagctg ctccccccct tccaagtgct gggaataaag gcgtgtgcct     240
ccacgcctgt ctctagttga catctttaag cttttaaggt tgtacaccta cttgctcagc     300
aactgagagc cagctgtgtg ccaaggtacc catgactgat gaagttggct ggggagagag     360
tctttgagat gagaggtctc tggtttgcca ggcagggctc ttaggacaac accagcaggg     420
cagggctctg ggaccacaga ttgagaaccc acaatggcct tgaaccttag acctgaatga     480
caggtgttgg tgggagaaca tgagcggaaa ttttcgtgga atgaacagct tctaagtcac     540
ctctactttc tcttaccggc ccagaggtct acacctcact ttggttttct aaattggctc     600 tccctgctt tttccatata tcaaacacat tcctggattc ctaacatctt tactgtgatt      660
cagggaccac cagaaagggc aggctggaaa ctgctgttct taggcagagt tccataagaa     720
acctcaggtc tacccttaa gacttagatg atctggagct ctcttcaatg atgtctacag      780
attgccctcc ccgctgcacc ccactccgca gccatatgaa gtatactagg ttggtgtggg     840
ggtaactgag aactacttat tgacatgtaa actggtcacc acagttcatt gtctcagcat     900
gttttgtctc cagatgaaca atagcctctc tctagtagag aagtgtcttg cacacaaaca     960
gaaacatttc ccagaagtgc cagtgtcgtt cattcatcct actttggttt aagtgtctga    1020
ttgttttttg ttttggaaac tgtctcattc tgtatgtagc ctaggctggt ctcaaactta    1080
gggtggtctt acctcagtct cctgagcccc gggcttgtgt cgtcacaccc agcttttctg    1140
tgttttgttt tttggttttg ttttgttttg aaacagggtt ttgctatgtg acttaggcat    1200
actatgtagc ctgggctggc cttgaactca tggacatctg cctctgtttc ctgagagcta    1260
gagttacaga tgtgtgtcac ttatgttcac tcttagtatc ctgtgattta tgttagatat    1320
tactgaaaat tattactaaa tcttgtcagt tgtagatacg atgggagaat gta           1373
```